United States Patent
Lee et al.

(10) Patent No.: US 6,346,605 B1
(45) Date of Patent: Feb. 12, 2002

(54) SIGNAL TRANSDUCER FOR THE TNF RECEPTOR SUPER FAMILY, AND USES THEREOF

(75) Inventors: Soo Young Lee; Yongwon Choi, both of New York, NY (US)

(73) Assignee: The Rockfeller University, New York, NY (US)

( * ) Notice: Subject to any disclaimer, the term of this patent is extended or adjusted under 35 U.S.C. 154(b) by 0 days.

(21) Appl. No.: 09/052,089

(22) Filed: Mar. 31, 1998

Related U.S. Application Data

(60) Provisional application No. 60/042,747, filed on Apr. 7, 1997, and provisional application No. 60/042,293, filed on Apr. 1, 1997.

(51) Int. Cl.[7] ............................................. C07K 14/47
(52) U.S. Cl. ........................... 530/350; 530/351; 514/2
(58) Field of Search ................................ 530/350, 351; 425/851; 514/2; 930/120, 144

(56) References Cited

U.S. PATENT DOCUMENTS 5,948,643 A * 9/1999 Rubinfeld et al. ......... 435/69.1

OTHER PUBLICATIONS

Amakawa et al.(1996), Cell,84:551–562.
Boldin et al.(1995), J. Biol. Chem.,270:7795–7798.
Boldin et al.(1996), Cell, 85:803–815.
Cao et al.(1996), Nature, 383:443–446.
Cheng et al.(1996), Genes Dev., 10:963–973.
Cheng et al.(1995), Science, 267:1494–1498.
Chinnaiyan et al.(1995), Cell, 81:505–512.
Gruss et al.(1994), Blood, 83:2045–2056.
Hsu et al.(1996), Cell, 84:299–308.
Hsu et al.(1995), Cell,81:495–504.
Hsu et al.(1996), Immunity, 4:387–396.
Hu et al.(1994), J. Biol. Chem. 269:30069–30072.
Itoh et al.(1993), J. Biol. Chem., 268:10932–10937.
Lee et al.(1996), J. Exp. Med., 183:669–674.
Lee et al.(1996), Proc. Natl. Acad. Sci. USA, 93:9699–9703.
Liu et al.(1996), Cell, 87:565–576.
Mclachlan et al.(1982), Nature, 299:226–231.
Landschulz et al.(1988), Science, 240:1759–1764.
Moisalos et al.(1995), Cell, 80:389–399.
Muzio et al.(1996), Cell, 85:817–827.
Nakano et al.(1996), J. of Biol. Chem., 271:14661–14664.
Park et al.(1996), Immunity, 4:583–591.
Regnier et al.(1995), J. Biol. Chem., 270:25715–25721.
Rothe et al.(1995), Cell, 83:1243–1252.
Rothe et al.(1995), Scince, 269:1424–1427.
Rothe et al.(1996), Proc. Natl. Acad. Sci. USA, 93:8241–8246.
Rothe et al.(1994), Cell, 78:681–692.
Sato et al.(1995), FEBS Letters, 358:113–118.
Smith et al.(1994), Cell, 76:959–962.
Song et al.(1995), Biochem. J., 809:825–829.
Song et al.(1996), Proc. Natl. Acad. Sci. USA, 93:6721–6725.
Tartaglia et al.(1993), Cell, 74:845–853.
Zheng et al.(1995), Nature, 377:348–351.

* cited by examiner

*Primary Examiner*—John Ulm
(74) *Attorney, Agent, or Firm*—Klauber & Jackson

(57) ABSTRACT

A novel component of the TRAF (TNF Receptor Associated Factor) signaling complex, designated TRIP (TRAF Interacting Protein) which associates with the TNFR2 or CD30 signaling complex through its interaction with the TRAF2 protein and influences signals responsible for cell activation, cell proliferation and cell death.

12 Claims, 13 Drawing Sheets

LEUCINE ZIPPER

FIG. 2D

```
mTRIP      4    LSLCTICSDFFFDHSRDVAAIHCGHTF-HLQCLIQWFETAPSRTCPQCRIQVG
hTRIP      4    RALCTICSDFFFDHSRDVAAMDCGHTF-HLQCLIQSFETAPSRTCPQCRIQVG mTRAF2    31    KYLCSACKNILRRPFQA---QCGHRY-CSFCLTSILSSGPQN-CAACVYEGL
mTRAF3    48    KYKCEKCRLVLCNPKQT---ECGHRF-CESCMAALLSSSSPK-CTACQ-ESI mc-IAP1  562    ERTCKVCMDREVSIVFI----PCGHLVVCQECAPSLRK-----CPICGRGTI
c-cbl    378    FQLCKICAENDKDVKIE----PCGHLM-CTSCLTSWQESEGQG-CPFCRCEIK
RING1     16    ELMCPICLDMLKNTMTTK---ECLHRF-CSDCIVTALRSGNKE-CPTCRKKLV
SS-A/Ro   13    EVTCPICLDPFVEPVSI----ECGHSF-CQECISQVGKGGGSV-CAVCRQRFL
C-RZF    237    YDVCAICLDEYEDGDKLRILPCSHAY-HCKCVDPWLTKTKKT-CPVCKQKVV
neu      698    SAECTICYENPIDSVLY---MCGHMCMCYDCAIEQWRGVGGGQCPLCRAVIR consensus       ....C..C..............CGH....C..C................C..C........
```

FIG. 8A

Human TRIP cDNA sequence
GTGCGGTGGAGCGAAATTTGAAGCAAGCGGAGGCGGGGCGCTCTACGAAGCCGGAC
CTGTAGCAGTTTCTTTGGCTGCCTGGGCCCCTTGAGTCCAGCCATCATGCCTATCC
GTGCTCTGTGCACTATCTGCTCCGACTTCTTCGATCACTCCCGCGACGTGGCCGCC
ATCCACTGCGGCCACACCTTCCACTTGCAGTGCCTAATTCAGTCCTTTGAGACAGC
ACCAAGTCGGACCTGCCCACAGTGCCGAATCCAGGTTGGCAAAAGAACCATTATCA
ATAAGCTCTTCTTTGATCTTGCCCAGGAGGAGGAGAATGTCTTGGATCGAGAATTC
TTAAAGAATGAACTGGACAATGTCAGAGCCCAGCTTTCCCAGAAAGACAAGGAGAA
ACGAGACAGCCAGGTCATCATCGACACTCTGCGGGATACGCTGGAAGAACGCAATG
CTACTGTGGTATCTCTGCAGCAGGCCTTGGGCAAGGCCGAGATGCTGTGCTCCACA
CTGAAAAAGCAGATGAAGTACTTAGAGCAGCAGCAGGATGAGACCAAACAAGCACA
AGAGGAGGCGGGCCGGCTCAGGAGCAAGATGAAGACCATGGAGCAGATTGAGCTTC
TACTCCAGAGCCAGCTCCCTGAGGTGGAGGAGATGATCCGAGACATGGGTGTGGGA
CAGTCAGCGGTGGAACAGCTGGCTGTGTACTGTGTGTCTCTCAAGAAAGAGTACGA
GAATCTAAAAGAGGCACGGAAGGCCTCAGGGGAGGTGGCTGACAAGCTGAGGAAGG
ATTTGTTTTCCTCCAGAAGCAAGTTGCAGACAGTCTACTCTGAATTGGATCAGGCC
AAGTTAGAACTGAAGTCAGCCCAGAAGGACTTACAGAGTGCTGACAAGGAAATCAT
GAGCCTGAAAAAGAAGCTAACGATGCTGCAGGAAACCTTGAACCTGCCACCAGTGG
CCAGTGAGACTGTCGACCGCCTGGTTTTAGAGAGCCCAGCCCCTGTGGAGGTGAAT
CTGAAGCTCCGCCGGCCATCCTTCCGTGATGATATTGATCTCAATGCTACCTTTGA
TGTGGATACTCCCCCAGCCCGGCCCTCCAGCTCCCAGCATGGTTACTACGAAAAAC
TTTGCCTAGAGAAGTCACACTCCCCAATTCAGGATGTCCCCAAGAAGATATGCAAA
GGCCCCAGGAAGGAGTCCCAGCTCTCACTGGGTGGCCAGAGCTGTGCAGGAGAGCC
AGATGAGGAACTGGTTGGTGCCTTCCCTATTTTTGTCCGGAATGCCATCCTAGGCC
AGAAACAGCCCAAAAGGCCCAGGTCAGAGTCCTCTTGCAGCAAAGATGTGGTAAGG
ACAGGCTTCGATGGGCTCGGTGGCCGGACAAAATTCATCCAGCCTACTGACACAGT
CATGATCCGCCCATTGCCTGTTAAGCCCAAGACCAAGGTTAAGCAGAGGGTGAGGG
TGAAGACCGTGCCTTCTCTCTTCCAGGCCAAGCTGGACACCTTCCTGTGGTCGTGA
GAACAGTGAGTCTGACCAATGGCCAGACACATGCCTGCAACTTGTAGGTCAAGGAC
TGTCCAGGCAGGGTTTGTGGACAGAGCCCTACTTTCGGGACCAGCCTGAGGTGTAA
GGGCAGACAAACAGGTGAGGGTGAGTGTGACACCCAGAGACTGCTCTTCCTGCCCT
CACCCTGCCCCACTCCTACGACTGGGAGCTGACATGACCAGCCCACTGATCCTGTC
AGCAGGTCCTGCTCTGTTGCCAGGCTCTTGTTTATAGCCATGATCAGATGTGGTCA
GACTCTTTCTGGGCCTGGAGACCACGGTCACTTGTTGACTGTCTCTGTGGACCAGA
GTGCTTGAGGCATCTCAGGCAGCCTCAGCCCAAGCTTCTACCTGCCTTTGACTTGC
TTCTAGCATAGCCTGGGCCAAGCAGGGTGGGGAATGGAGGATAGACATGGGATGTA
TGGAGAGGATGGAAGATTTTCCCGAAAAAAAAAAAAAAAAAAAAAA

FIG. 8B murine TRIP cDNa sequence
GGCACGAGGTGCGGTGGAGCGAAATTTGAAGGAACCGGAGCGGTGGCCGGTTCCAC
CAAACTGTGTCTGTCTCTGGCAGCTGGTTCCCTGGGCTGCTTGAGTCGAGCCATCA
TGCCTATCCTCTCTCTGTGCACTATCTGCTCCGACTTCTTCGATCACTCCCGTGAC
GTGGCTGCCATCCACTGTGGCCACACTTTTCATCTGCAATGCCTAATCCAGTGGTT
TGAGACAGCACCAAGTCGGACCTGCCCACAGTGTAGAATCCAGGTTGGCAAAAGA
CTATTATAAACAAACTTTTCTTTGACCTCGCCCAGGAAGAGGAGAATGTCTTGGAT
GCAGAATTCTTAAAGAATGAACTGGACAGCGTCAAAGCTCAGCTTTCCAGAAAGA
CAGGGAGAAACGGGACAGCCAGGCCATTATCGACACTCTACGGGACACCCTGGAAG
AACGCAATGCTACCGTGGAGTCCCTACAGAACGCCTTAAACAAGGCAGAGATGCTG
TGTTCCACCCTGAAAAAACAGATGAAGTTCCTGGAGCAGCGGCAGGATGAGACCAA
ACAAGCTCGGGAGGAGGCCCACCGACTCAAGTGCAAGATGAAAACCATGGAGCAAA
TTGAGCTCCTACTCCAGAGCCAGCGTTCTGAGGTGGAGGAGATGATTCGAGACATG
GGTGTGGGACAGTCAGCGGTGGAGCAGCTGGCTGTGTACTGCGTGTCCCTCAAGAA
AGAGTATGAGAATCTGAAGGAAGCTCGGAAGGCCACAGGGGAACTGGCTGACAGGT
TGAAGAAGGATTTGGTGTCCTCTAGGAGCAAGTTGAAGACTCTCAACACTGAGCTG
GATCAGGCCAAGTTAGAACTGAGGTCAGCCCAGAAGGACTTACAAAGTGCTGACCA
GGAGATCACGAGCCTAAGAAAGAAGCTGATGATCCTCCAGGGAACCTTGAGCCTGC
CTCCGCGTACCAATGAGACGGTCAGCCGCCTGGTTTTTGAGAGCCCAGCCCCTGTG
GAGATGATGAACCCGAGGCTTCACCAGCCACCCTTCGGTGATGAGATTGATCTCAA
TACCACCTTTGATGTAAATACCCCTCCAACCCAGACCTCTGGCTCCCAGCATTGCC
TCCCCAAGAAGCTGTGCCTGGAGAGGGCACGCTCTCCCATGCAGAATGTCCTCAAG
AAGGTGCACAAAGTCTCCAAGCCGGAGTCCCAGCTCTCACTGGGTGGCCAGCGATG
TGTAGGAGAGCTAGATGAGGAACTGGCTGGTGCCTTCCCTCTCTTCATCCGGAATG
CTGTCCTGGGTCAGAAACAGCCCAACAGGACCACAGCAGAATCCCGAAGCAGCACA
GATGTGGTAAGAATAGGCTTTGATGGGCTTGGAGGACGAACAAAATTCATCCAGCC
TAGGGACACAACCATTATCCGACCAGTGCCTGTTAAGTCCAAGGCCAAGAGTAAAC
AGAAAGTGAGAATAAAGACTGTGAGTTCTGCCTCCCAGCCCAAGCTGGATACCTTC
TTATGTCAGTGAACGGTGACCAGAGTGATGTTTGCAATTAGTGGGCCAAGACCTGG
CTAACCGGAAGTGTTTTTGGAAGATGGCTCCTCTTGGACCAGTCCAAGAGAGATGC
CCAGAAAACACACTTCCTGTGTTCACTGCGCCCTGCACCACACTGGGAAGCCACAT
GACCAGTTTACTGTTCCGATCAGCAGGGCCTACTTCCAGTTGCAGGGTTTTGCTTA
TAGCTACAACCAGGTGTGGCTGGACTCCTTTTGTTTTTATAGAACAGGGTCACATT
GACTCTAAGTGGATGGGAGTGCTGGAGGATCCTATGCAGGCTGGAGGACCCTGCGC
TTGAACTCCTGCCTGCCTCCAGCTTATTGCTTGAAATTATGGGGTGAGGTGGTGAT
AGGGAAAGGTTGGGGAAGTTTTCTGTGTAAAATAAAAGGGATCTTTTCTTCAAAA
AAAAAAAAAAAAAA

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
       (A) LENGTH: 469 amino acids
       (B) TYPE: amino acid
       (C) STRANDEDNESS: single
       (D) TOPOLOGY: linear (ii) MOLECULE TYPE: protein (iii) HYPOTHETICAL: NO (v) FRAGMENT TYPE: <Unknown>

(vi) ORIGINAL SOURCE:
       (A) ORGANISM: Homo sapiens (xi) SEQUENCE DESCRIPTION: SEQ ID NO: 1:

Met Pro Ile Arg Ala Leu Cys Thr Ile Cys Ser Asp Phe Phe Asp Hi
1               5                   10                  15

Ser Arg Asp Val Ala Ala Ile His Cys Gly His Thr Phe His Leu Gl
                20                  25                  30

Cys Leu Ile Gln Ser Phe Glu Thr Ala Pro Ser Arg Thr Cys Pro Gl
            35                  40                  45

Cys Arg Ile Gln Val Gly Lys Arg Thr Ile Ile Asn Lys Leu Phe Ph
        50                  55                  60

Asp Leu Ala Gln Glu Glu Glu Asn Val Leu Asp Arg Glu Phe Leu Ly
65                  70                  75                  80

Asn Glu Leu Asp Asn Val Arg Ala Gln Leu Ser Gln Lys Asp Lys Gl
                85                  90                  95

Lys Arg Asp Ser Gln Val Ile Ile Asp Thr Leu Arg Asp Thr Leu Gl
            100                 105                 110

Glu Arg Asn Ala Thr Val Val Ser Leu Gln Gln Ala Leu Gly Lys Al
        115                 120                 125

Glu Met Leu Cys Ser Thr Leu Lys Lys Gln Met Lys Tyr Leu Glu Gl

-continued

```
              130                 135                 140
Gln Gln Asp Glu Thr Lys Gln Ala Gln Glu Ala Gly Arg Leu Ar
145                 150                 155                 160
Ser Lys Met Lys Thr Met Glu Gln Ile Glu Leu Leu Gln Ser Gl
                165                 170                 175
Leu Pro Glu Val Glu Glu Met Ile Arg Asp Met Gly Val Gly Gln Se
                180                 185                 190
Ala Val Glu Gln Leu Ala Val Tyr Cys Val Ser Leu Lys Lys Glu Ty
                195                 200                 205
Glu Asn Leu Lys Glu Ala Arg Lys Ala Ser Gly Glu Val Ala Asp Ly
                210                 215                 220
Leu Arg Lys Asp Leu Phe Ser Ser Arg Ser Lys Leu Gln Thr Val Ty
225                 230                 235                 240
Ser Glu Leu Asp Gln Ala Lys Leu Glu Leu Lys Ser Ala Gln Lys As
                245                 250                 255
Leu Gln Ser Ala Asp Lys Glu Ile Met Ser Leu Lys Lys Lys Leu Th
                260                 265                 270
Met Leu Gln Glu Thr Leu Asn Leu Pro Pro Val Ala Ser Glu Thr Va
                275                 280                 285
Asp Arg Leu Val Leu Glu Ser Pro Ala Pro Val Glu Val Asn Leu Ly
                290                 295                 300
Leu Arg Arg Pro Ser Phe Arg Asp Asp Ile Asp Leu Asn Ala Thr Ph
305                 310                 315                 320
Asp Val Asp Thr Pro Pro Ala Arg Pro Ser Ser Gln His Gly Ty
                325                 330                 335
Tyr Glu Lys Leu Cys Leu Glu Lys Ser His Ser Pro Ile Gln Asp Va
                340                 345                 350
Pro Lys Lys Ile Cys Lys Gly Pro Arg Lys Glu Ser Gln Leu Ser Le
                355                 360                 365
Gly Gly Gln Ser Cys Ala Gly Glu Pro Asp Glu Glu Leu Val Gly Al
                370                 375                 380
Phe Pro Ile Phe Val Arg Asn Ala Ile Leu Gly Gln Lys Gln Pro Ly
385                 390                 395                 400
Arg Pro Arg Ser Glu Ser Ser Cys Ser Lys Asp Val Val Arg Thr Gl
                405                 410                 415
Phe Asp Gly Leu Gly Gly Arg Thr Lys Phe Ile Gln Pro Thr Asp Th
                420                 425                 430
Val Met Ile Arg Pro Leu Pro Val Lys Pro Lys Thr Lys Val Lys Gl
                435                 440                 445
Arg Val Arg Val Lys Thr Val Pro Ser Leu Phe Gln Ala Lys Leu As
    450                 455                 460
Thr Phe Leu Trp Ser
465
```

(2) INFORMATION FOR SEQ ID NO: 2:

(i) SEQUENCE CHARACTERISTICS:
        (A) LENGTH: 470 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE: <Unknown>

(vi) ORIGINAL SOURCE:
    (A) ORGANISM: mouse (xi) SEQUENCE DESCRIPTION: SEQ ID NO: 2:

```
Met Pro Ile Leu Ser Leu Cys Thr Ile Cys Ser Asp Phe Phe Asp Hi
1               5                   10                  15

Ser Arg Asp Val Ala Ala Ile His Cys Gly His Thr Phe His Leu Gl
                20                  25                  30

Cys Leu Ile Gln Trp Phe Glu Thr Ala Pro Ser Arg Thr Cys Pro Gl
            35                  40                  45

Cys Arg Ile Gln Val Gly Lys Lys Thr Ile Ile Asn Lys Leu Phe Ph
        50                  55                  60

Asp Leu Ala Gln Glu Glu Asn Val Leu Asp Ala Glu Phe Leu Ly
65                  70                  75                  80

Asn Glu Leu Asp Ser Val Lys Ala Gln Leu Ser Gln Lys Asp Arg Gl
                85                  90                  95

Lys Arg Asp Ser Gln Ala Ile Ile Asp Thr Leu Arg Asp Thr Leu Gl
            100                 105                 110

Glu Arg Asn Ala Thr Val Glu Ser Leu Gln Asn Ala Leu Asn Lys Al
        115                 120                 125

Glu Met Leu Cys Ser Thr Leu Lys Lys Gln Met Lys Phe Leu Glu Gl
    130                 135                 140

Arg Gln Asp Glu Thr Lys Gln Ala Arg Glu Glu Ala His Arg Leu Ly
145                 150                 155                 160

Cys Lys Met Lys Thr Met Glu Gln Ile Glu Leu Leu Gln Ser Gl
                165                 170                 175

Arg Ser Glu Val Glu Glu Met Ile Arg Asp Met Gly Val Gly Gln Se
                180                 185                 190

Ala Val Glu Gln Leu Ala Val Tyr Cys Val Ser Leu Lys Lys Glu Ty
            195                 200                 205

Glu Asn Leu Lys Glu Ala Arg Lys Ala Thr Gly Glu Leu Ala Asp Ar
        210                 215                 220

Leu Lys Lys Asp Leu Val Ser Ser Arg Ser Lys Leu Lys Thr Leu As
225                 230                 235                 240

Thr Glu Leu Asp Gln Ala Lys Leu Glu Leu Arg Ser Ala Gln Lys As
                245                 250                 255

Leu Gln Ser Ala Asp Gln Glu Ile Thr Ser Leu Arg Lys Lys Ser As
            260                 265                 270

Asp Pro Pro Gly Asn Leu Glu Pro Ala Ser Ala Thr Asn Glu Thr Va
        275                 280                 285

Ser Arg Leu Val Phe Glu Ser Pro Ala Pro Val Glu Met Met Asn Pr
    290                 295                 300

Arg Leu His Gln Pro Pro Phe Gly Asp Glu Ile Asp Leu Asn Thr Th
305                 310                 315                 320

Phe Asp Val Asn Thr Pro Pro Thr Gln Thr Ser Gly Ser Gln His Cy
                325                 330                 335

Leu Pro Lys Lys Leu Cys Leu Glu Arg Ala Arg Ser Pro Met Gln As
            340                 345                 350

Val Leu Lys Lys Val His Lys Val Ser Lys Pro Glu Ser Gln Leu Se
        355                 360                 365

Leu Gly Gly Gln Arg Cys Val Gly Glu Leu Asp Glu Glu Leu Ala Gl
    370                 375                 380

Ala Phe Pro Leu Phe Ile Arg Asn Ala Val Leu Gly Gln Lys Gln Pr
```

```
                385                 390                 395                 400
Asn Arg Thr Thr Ala Glu Ser Arg Ser Ser Thr Asp Val Val Arg Il
                        405                 410                 415

Gly Phe Asp Gly Leu Gly Gly Arg Thr Lys Phe Ile Gln Pro Arg As
                        420                 425                 430

Thr Thr Ile Ile Arg Pro Val Pro Val Lys Ser Lys Ala Lys Ser Ly
                        435                 440                 445

Gln Lys Val Arg Ile Lys Thr Val Ser Ser Ala Ser Gln Pro Lys Le
        450                 455                 460

Asp Thr Phe Leu Cys Gln
465                 470
```

(2) INFORMATION FOR SEQ ID NO: 3:

(i) SEQUENCE CHARACTERISTICS:
        (A) LENGTH: 220 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Homo sapiens (xi) SEQUENCE DESCRIPTION: SEQ ID NO: 3:

```
Arg Thr Ile Ile Asn Lys Leu Phe Phe Asp Leu Ala Gln Glu Glu Gl
1                   5                   10                  15

Asn Val Leu Asp Arg Glu Phe Leu Lys Asn Glu Leu Asp Asn Val Ar
                20                  25                  30

Ala Gln Leu Ser Gln Lys Asp Lys Glu Lys Arg Asp Ser Gln Val Il
            35                  40                  45

Ile Asp Thr Leu Arg Asp Thr Leu Glu Glu Arg Asn Ala Thr Val Va
        50                  55                  60

Ser Leu Gln Gln Ala Leu Gly Lys Ala Glu Met Leu Cys Ser Thr Le
65                  70                  75                  80

Lys Lys Gln Met Lys Tyr Leu Glu Gln Gln Asp Glu Thr Lys Gl
                85                  90                  95

Ala Gln Glu Glu Ala Gly Arg Leu Arg Ser Lys Met Lys Thr Met Gl
                100                 105                 110

Gln Ile Glu Leu Leu Leu Gln Ser Gln Leu Pro Glu Val Glu Glu Me
            115                 120                 125

Ile Arg Asp Met Gly Val Gly Gln Ser Ala Val Glu Gln Leu Ala Va
        130                 135                 140

Tyr Cys Val Ser Leu Lys Lys Glu Tyr Glu Asn Leu Lys Glu Ala Ar
145                 150                 155                 160

Lys Ala Ser Gly Glu Val Ala Asp Lys Leu Arg Lys Asp Leu Phe Se
                165                 170                 175

Ser Arg Ser Lys Leu Gln Thr Val Tyr Ser Glu Leu Asp Gln Ala Ly
            180                 185                 190

Leu Glu Leu Lys Ser Ala Gln Lys Asp Leu Gln Ser Ala Asp Lys Gl
        195                 200                 205

Ile Met Ser Leu Lys Lys Lys Leu Thr Met Leu Gln
210                 215                 220
```

(2) INFORMATION FOR SEQ ID NO: 4:

(i) SEQUENCE CHARACTERISTICS:
        (A) LENGTH: 220 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: mouse (xi) SEQUENCE DESCRIPTION: SEQ ID NO: 4:

```
Lys Thr Ile Ile Asn Lys Leu Phe Phe Asp Leu Ala Gln Glu Gl
1               5                   10                  15

Asn Val Leu Asp Ala Glu Phe Leu Lys Asn Glu Leu Asp Ser Val Ly
                20                  25                  30

Ala Gln Leu Ser Gln Lys Asp Arg Glu Lys Arg Asp Ser Gln Ala Il
            35                  40                  45

Ile Asp Thr Leu Arg Asp Thr Leu Glu Glu Arg Asn Ala Thr Val Gl
50                  55                  60

Ser Leu Gln Asn Ala Leu Asn Lys Ala Glu Met Leu Cys Ser Thr Le
65                  70                  75                  80

Lys Lys Gln Met Lys Phe Leu Glu Gln Arg Gln Asp Glu Thr Lys Gl
                85                  90                  95

Ala Arg Glu Glu Ala His Arg Leu Lys Cys Lys Met Lys Thr Met Gl
            100                 105                 110

Gln Ile Glu Leu Leu Leu Gln Ser Gln Arg Ser Glu Val Glu Glu Me
            115                 120                 125

Ile Arg Asp Met Gly Val Gly Gln Ser Ala Val Glu Gln Leu Ala Va
130                 135                 140

Tyr Cys Val Ser Leu Lys Lys Glu Tyr Glu Asn Leu Lys Glu Ala Ar
145                 150                 155                 160

Lys Ala Thr Gly Glu Leu Ala Asp Arg Leu Lys Lys Asp Leu Val Se
                165                 170                 175

Ser Arg Ser Lys Leu Lys Thr Leu Asn Thr Glu Leu Asp Gln Ala Ly
            180                 185                 190

Leu Glu Leu Arg Ser Ala Gln Lys Asp Leu Gln Ser Ala Asp Gln Gl
            195                 200                 205

Ile Thr Ser Leu Arg Lys Lys Ser Asp Asp Pro Pro
210                 215                 220
```

(2) INFORMATION FOR SEQ ID NO: 5:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Homo sapiens (xi) SEQUENCE DESCRIPTION: SEQ ID NO: 5:

Arg Ala Leu Cys Thr Ile Cys Ser Asp Phe Phe Asp His Ser Arg As
1               5                   10                  15

Val Ala Ala Met Asp Cys Gly His Thr Phe His Leu Gln Cys Leu Il
            20                  25                  30

Gln Ser Phe Glu Thr Ala Pro Ser Arg Thr Cys Pro Gln Cys Arg Il
        35                  40                  45

Gln Val Gly
    50

(2) INFORMATION FOR SEQ ID NO: 6:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: mouse (xi) SEQUENCE DESCRIPTION: SEQ ID NO: 6:

Leu Ser Leu Cys Thr Ile Cys Ser Asp Phe Phe Asp His Ser Arg As
1               5                   10                  15

Val Ala Ala Ile His Cys Gly His Thr Phe His Leu Gln Cys Leu Il
            20                  25                  30

Gln Trp Phe Glu Thr Ala Pro Ser Arg Thr Cys Pro Gln Cys Arg Il
        35                  40                  45

Gln Val Gly
    50

(2) INFORMATION FOR SEQ ID NO: 7:

(i) SEQUENCE CHARACTERISTICS:
        (A) LENGTH: 2007 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: Homo sapiens (xi) SEQUENCE DESCRIPTION: SEQ ID NO: 7:

```
GTGCGGTGGA GCGAAATTTG AAGCAAGCGG AGGCGGGGCG CTCTACGAAG CCGGACCTGT      60

AGCAGTTTCT TTGGCTGCCT GGGCCCCTTG AGTCCAGCCA TCATGCCTAT CCGTGCTCT      120

TGCACTATCT GCTCCGACTT CTTCGATCAC TCCCGCGACG TGGCCGCCAT CCACTGCGG      180

CACACCTTCC ACTTGCAGTG CCTAATTCAG TCCTTTGAGA CAGCACCAAG TCGGACCTG      240

CCACAGTGCC GAATCCAGGT TGGCAAAAGA ACCATTATCA ATAAGCTCTT CTTTGATCT      300

GCCCAGGAGG AGGAGAATGT CTTGGATCGA GAATTCTTAA AGAATGAACT GGACAATGT      360

AGAGCCCAGC TTTCCCAGAA AGACAAGGAG AAACGAGACA GCCAGGTCAT CATCGACAC      420
```

```
CTGCGGGATA CGCTGGAAGA ACGCAATGCT ACTGTGGTAT CTCTGCAGCA GGCCTTGGG      480

AAGGCCGAGA TGCTGTGCTC CACACTGAAA AAGCAGATGA AGTACTTAGA GCAGCAGCA      540

GATGAGACCA AACAAGCACA AGAGGAGGCG GGCCGGCTCA GGAGCAAGAT GAAGACCAT      600

GAGCAGATTG AGCTTCTACT CCAGAGCCAG CTCCCTGAGG TGGAGGAGAT GATCCGAGA      660

ATGGGTGTGG ACAGTCAGC GGTGGAACAG CTGGCTGTGT ACTGTGTGTC TCTCAAGAA      720

GAGTACGAGA ATCTAAAAGA GGCACGGAAG GCCTCAGGGG AGGTGGCTGA CAAGCTGAG      780

AAGGATTTGT TTTCCTCCAG AAGCAAGTTG CAGACAGTCT ACTCTGAATT GGATCAGGC      840

AAGTTAGAAC TGAAGTCAGC CCAGAAGGAC TTACAGAGTG CTGACAAGGA AATCATGAG      900

CTGAAAAAGA AGCTAACGAT GCTGCAGGAA ACCTTGAACC TGCCACCAGT GGCCAGTGA      960

ACTGTCGACC GCCTGGTTTT AGAGAGCCCA GCCCCTGTGG AGGTGAATCT GAAGCTCC     1020

CGGCCATCCT TCCGTGATGA TATTGATCTC AATGCTACCT TTGATGTGGA TACTCCCC     1080

GCCCGGCCCT CCAGCTCCCA GCATGGTTAC TACGAAAAAC TTTGCCTAGA GAAGTCAC     1140

TCCCCAATTC AGGATGTCCC CAAGAAGATA TGCAAAGGCC CCAGGAAGGA GTCCCAGC     1200

TCACTGGGTG CCAGAGCTG TGCAGGAGAG CCAGATGAGG AACTGGTTGG TGCCTTCC     1260

ATTTTTGTCC GGAATGCCAT CCTAGGCCAG AAACAGCCCA AAAGGCCCAG GTCAGAGT     1320

TCTTGCAGCA AAGATGTGGT AAGGACAGGC TTCGATGGGC TCGGTGGCCG GACAAAAT     1380

ATCCAGCCTA CTGACACAGT CATGATCCGC CCATTGCCTG TTAAGCCCAA GACCAAGG     1440

AAGCAGAGGG TGAGGGTGAA GACCGTGCCT TCTCTCTTCC AGGCCAAGCT GGACACCT     1500

CTGTGGTCGT GAGAACAGTG AGTCTGACCA ATGGCCAGAC ACATGCCTGC AACTTGTA     1560

TCAAGGACTG TCCAGGCAGG GTTTGTGGAC AGAGCCCTAC TTTCGGGACC AGCCTGAG     1620

GTAAGGGCAG ACAAACAGGT GAGGGTGAGT GTGACACCCA GAGACTGCTC TTCCTGCC     1680

CACCCTGCCC CACTCCTACG ACTGGGAGCT GACATGACCA GCCCACTGAT CCTGTCAG     1740

GGTCCTGCTC TGTTGCCAGG CTCTTGTTTA TAGCCATGAT CAGATGTGGT CAGACTCT     1800

CTGGGCCTGG AGACCACGGT CACTTGTTGA CTGTCTCTGT GGACCAGAGT GCTTGAGG     1860

TCTCAGGCAG CCTCAGCCCA AGCTTCTACC TGCCTTTGAC TTGCTTCTAG CATAGCCT     1920

GCCAAGCAGG GTGGGGAATG GAGGATAGAC ATGGGATGTA TGGAGAGGAT GGAAGATT     1980

CCCGAAAAAA AAAAAAAAAA AAAAAA                                        2007
```

(2) INFORMATION FOR SEQ ID NO: 8:

(i) SEQUENCE CHARACTERISTICS:
        (A) LENGTH: 1975 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: mouse (xi) SEQUENCE DESCRIPTION: SEQ ID NO: 8:

```
GGCACGAGGT GCGGTGGAGC GAAATTTGAA GGAACCGGAG CGGTGGCCGG TTCCACCAAA      60

CTGTGTCTGT CTCTGGCAGC TGGTTCCCTG GGCTGCTTGA GTCGAGCCAT CATGCCTAT      120

CTCTCTCTGT GCACTATCTG CTCCGACTTC TTCGATCACT CCCGTGACGT GGCTGCCAT      180

CACTGTGGCC ACACTTTTCA TCTGCAATGC CTAATCCAGT GGTTTGAGAC AGCACCAAG      240
```

-continued

```
CGGACCTGCC CACAGTGTAG AATCCAGGTT GGCAAAAAGA CTATTATAAA CAAACTTTT        300

TTTGACCTCG CCCAGGAAGA GGAGAATGTC TTGGATGCAG AATTCTTAAA GAATGAACT        360

GACAGCGTCA AAGCTCAGCT TTCCCAGAAA GACAGGGAGA AACGGGACAG CCAGGCCAT        420

ATCGACACTC TACGGGACAC CCTGGAAGAA CGCAATGCTA CCGTGGAGTC CCTACAGAA        480

GCCTTAAACA AGGCAGAGAT GCTGTGTTCC ACCCTGAAAA AACAGATGAA GTTCCTGGA        540

CAGCGGCAGG ATGAGACCAA ACAAGCTCGG GAGGAGGCCC ACCGACTCAA GTGCAAGAT        600

AAAACCATGG AGCAAATTGA GCTCCTACTC CAGAGCCAGC GTTCTGAGGT GGAGGAGAT        660

ATTCGAGACA TGGGTGTGGG ACAGTCAGCG GTGGAGCAGC TGGCTGTGTA CTGCGTGTC        720

CTCAAGAAAG AGTATGAGAA TCTGAAGGAA GCTCGGAAGG CCACAGGGGA ACTGGCTGA        780

AGGTTGAAGA AGGATTTGGT GTCCTCTAGG AGCAAGTTGA AGACTCTCAA CACTGAGCT        840

GATCAGGCCA AGTTAGAACT GAGGTCAGCC CAGAAGGACT TACAAAGTGC TGACCAGGA        900

ATCACGAGCC TAAGAAAGAA GTCTGATGAT CCTCCAGGGA ACCTTGAGCC TGCCTCCGC        960

ACCAATGAGA CGGTCAGCCG CCTGGTTTTT GAGAGCCCAG CCCCTGTGGA GATGATGA       1020

CCGAGGCTTC ACCAGCCACC CTTCGGTGAT GAGATTGATC TCAATACCAC CTTTGATG       1080

AATACCCCTC CAACCCAGAC CTCTGGCTCC CAGCATTGCC TCCCCAAGAA GCTGTGCC       1140

GAGAGGGCAC GCTCTCCCAT GCAGAATGTC CTCAAGAAGG TGCACAAAGT CTCCAAGC       1200

GAGTCCCAGC TCTCACTGGG TGGCCAGCGA TGTGTAGGAG AGCTAGATGA GGAACTGG       1260

GGTGCCTTCC CTCTCTTCAT CCGGAATGCT GTCCTGGGTC AGAAACAGCC CAACAGGA       1320

ACAGCAGAAT CCCGAAGCAG CACAGATGTG GTAAGAATAG GCTTTGATGG GCTTGGAG       1380

CGAACAAAAT TCATCCAGCC TAGGGACACA ACCATTATCC GACCAGTGCC TGTTAAGT       1440

AAGGCCAAGA GTAAACAGAA AGTGAGAATA AAGACTGTGA GTTCTGCCTC CCAGCCCA       1500

CTGGATACCT TCTTATGTCA GTGAACGGTG ACCAGAGTGA TGTTTGCAAT TAGTGGGC       1560

AGACCTGGCT AACCGGAAGT GTTTTTGGAA GATGGCTCCT CTTGGACCAG TCCAAGAG       1620

ATGCCCAGAA AACACACTTC CTGTGTTCAC TGCGCCCTGC ACCACACTGG GAAGCCAC       1680

GACCAGTTTA CTGTTCCGAT CAGCAGGGCC TACTTCCAGT TGCAGGGTTT TGCTTATA       1740

TACAACCAGG TGTGGCTGGA CTCCTTTTGT TTTTATAGAA CAGGGTCACA TTGACTCT       1800

GTGGATGGGA GTGCTGGAGG ATCCTATGCA GGCTGGAGGA CCCTGCGCTT GAACTCCT       1860

CTGCCTCCAG CTTATTGCTT GAAATTATGG GGTGAGGTGG TGATAGGGAA AGGTTGGG       1920

AGTTTTCTGT GTAAAATAAA AAGGGATCTT TTCTTCAAAA AAAAAAAAA AAAAA          1975
```

(2) INFORMATION FOR SEQ ID NO: 9:

(i) SEQUENCE CHARACTERISTICS:
        (A) LENGTH: 47 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 9:

```
Lys Tyr Leu Cys Ser Ala Cys Lys Asn Ile Leu Arg Arg Pro Phe Gl
1               5                   10                  15
```

```
Ala Gln Cys Gly His Arg Tyr Cys Ser Phe Cys Leu Thr Ser Ile Le
            20                  25                  30

Ser Ser Gly Pro Gln Asn Cys Ala Ala Cys Val Tyr Glu Gly Leu
            35                  40                  45
```

(2) INFORMATION FOR SEQ ID NO: 10:

(i) SEQUENCE CHARACTERISTICS:
        (A) LENGTH: 46 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 10:

```
Lys Tyr Lys Cys Glu Lys Cys Arg Leu Val Leu Cys Asn Pro Lys Gl
1               5                   10                  15

Thr Glu Cys Gly His Arg Phe Cys Glu Ser Cys Met Ala Ala Leu Le
            20                  25                  30

Ser Ser Ser Ser Pro Lys Cys Thr Ala Cys Gln Glu Ser Ile
            35                  40                  45
```

(2) INFORMATION FOR SEQ ID NO: 11:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 11:

```
Glu Arg Thr Cys Lys Val Cys Met Asp Arg Glu Val Ser Ile Val Ph
1               5                   10                  15

Ile Pro Cys Gly His Leu Val Val Cys Gln Glu Cys Ala Pro Ser Le
            20                  25                  30

Arg Lys Cys Pro Ile Cys Gly Arg Gly Thr Ile
            35                  40
```

(2) INFORMATION FOR SEQ ID NO: 12:

(i) SEQUENCE CHARACTERISTICS:
        (A) LENGTH: 47 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 12:

```
Phe Gln Leu Cys Lys Ile Cys Ala Glu Asn Asp Lys Asp Val Lys Il
1               5                   10                  15

Glu Pro Cys Gly His Leu Met Cys Thr Ser Cys Leu Thr Ser Trp Gl
```

```
                    20                  25                  30
Glu Ser Glu Gly Gln Gly Cys Pro Phe Cys Arg Cys Glu Ile Lys
         35                  40                  45

(2) INFORMATION FOR SEQ ID NO: 13:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 13:

Glu Leu Met Cys Pro Ile Cys Leu Asp Met Leu Lys Asn Thr Met Th
1               5                   10                  15
Thr Lys Glu Cys Leu His Arg Phe Cys Ser Asp Cys Ile Val Thr Al
            20                  25                  30
Leu Arg Ser Gly Asn Lys Glu Cys Pro Thr Cys Arg Lys Lys Leu Va
         35                  40                  45

(2) INFORMATION FOR SEQ ID NO: 14:

(i) SEQUENCE CHARACTERISTICS:
        (A) LENGTH: 47 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 14:

Glu Val Thr Cys Pro Ile Cys Leu Asp Pro Phe Val Glu Pro Val Se
1               5                   10                  15
Ile Glu Cys Gly His Ser Phe Cys Gln Glu Cys Ile Ser Gln Val Gl
            20                  25                  30
Lys Gly Gly Gly Ser Val Cys Ala Val Cys Arg Gln Arg Phe Leu
         35                  40                  45

(2) INFORMATION FOR SEQ ID NO: 15:

(i) SEQUENCE CHARACTERISTICS:
        (A) LENGTH: 50 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 15:

Tyr Asp Val Cys Ala Ile Cys Leu Asp Glu Tyr Glu Asp Gly Asp Ly
1               5                   10                  15
Leu Arg Ile Leu Pro Cys Ser His Ala Tyr His Cys Lys Cys Val As
            20                  25                  30
```

```
Pro Trp Leu Thr Lys Thr Lys Lys Thr Cys Pro Val Cys Lys Gln Ly
        35                  40                  45

Val Val
    50

(2) INFORMATION FOR SEQ ID NO: 16:

(i) SEQUENCE CHARACTERISTICS:
        (A) LENGTH: 49 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 16:

Ser Ala Glu Cys Thr Ile Cys Tyr Glu Asn Pro Ile Asp Ser Val Le
1               5                  10                  15

Tyr Met Cys Gly His Met Cys Met Cys Tyr Asp Cys Ala Ile Glu Gl
            20                  25                  30

Trp Arg Gly Val Gly Gly Gly Gln Cys Pro Leu Cys Arg Ala Val Il
            35                  40                  45

Arg
```

SIGNAL TRANSDUCER FOR THE TNF RECEPTOR SUPER FAMILY, AND USES THEREOF

The priority of U.S. Provisional Applications No. 60/042,293, filed Apr. 1, 1997, and No. 60/042,747, filed Apr. 7, 1997, is claimed.

TECHNICAL FIELD OF THE INVENTION

The present invention relates generally to isolation and utilization of novel proteins, and more particularly to a unique receptor-signaling-complex component referred to as the tumor necrosis factor receptor associated factor interacting protein.

BACKGROUND OF THE INVENTION

Members of the TNFR (Tumor Necrosis Factor Receptor) superfamily play important roles in the induction of diverse signals leading to cell growth, activation and apoptosis. Smith et al., Cell, 76:959–962 (1994). Whether the signals induced by a given receptor leads to a cell's activation or death is highly cell-type specific and tightly regulated during differentiation of the cell. For example, the TNFRs can exert co-stimulatory signals for proliferation of naive lymphocytes, but can also induce death signals required for deletion of activated T lymphocytes. Smith et al., Cell, Id.

The cytoplasmic domains of these receptors lack intrinsic catalytic activity and generally exhibit no significant homology to each other or to other known proteins. Exceptions to this include Fas(CD95) and TNF-R1 which share significant homology within an 80 amino acid region of their cytoplasmic tails, referred to in the art as the "death domain." Tartaglia et al., Cell, 74:845–853 (1993); Itoh et al., J. Biol. Chem. 268:10932–10937 (1993). Therefore, the TNFR family members are believed to initiate different signal transduction pathways by recruiting different types of intracellular signal transducers to the receptor complex. Smith et al., Cell, Id.

Several types of intracellular signal transducers have been identified that initiate distinct signal transduction pathways when recruited to the members of TNFR superfamily. Rothe et al., Cell, 78:681–692 (1994); Cheng et al., Science, 267:1494–1498 (1995); Nakano et al., J. of Biol. Chem., 271: 14661–14664 (1996). Recent biochemical and molecular studies show that a class of signal transducing molecules are recruited to Fas(CD95) or TNFR1 via interaction of the death domains. Chinnaiyan et al., Cell, 81:505–512 (1995); Boldin et al., J. Biol. Chem., 270:7795–7798 (1995); Hsu et al., Cell, 81:495–504, (1995). For example, Fas(CD95) and TNFR1 recruit FADD(MORT1)/RIP or TRADD/FADD (MORT1)/RIP through the interactions of their respective death domains. Itoh et al., J. Biol. Chem., Id.; Tartaglia et al., Cell, Id.; Hsu et al., Immunity, 4:387–396 (1996). The clustering of these signal transducers leads to the recruitment of FLICE/MACH, and subsequently, to cell death. Muzio et al., Cell, 85:817–827 (1996); Boldin et al., Cell, 81: 803–815 (1996).

The TNFR family members can also recruit a second class of signal transducers called TRAF (Tumor necrosis factor Receptor Associated Factor), some of which are responsible for the activation of NF-kB or JNK. Hsu et al., Cell, 84:299–308 (1996); Liu et al., Cell, 87:565–576. TRAF proteins were identified by their biochemical ability to interact with TNFR2, CD40, CD30 or LT-βR receptors which interact directly with TRAFs via a short stretch of amino acids within their cytoplasmic tails but which do not interact with the death domain containing proteins. Sato et al., FEBS Letters, 358:113–118 (1995); Song et al., Biochem. J., 809:825–829 (1995); Lee et al., J. Exp. Med., 183:669–674 (1996).

Distinct members of the TPAF family have been identified as signaling components of the TNFR family. All TRAF members contain a conserved TRAF domain, approximately 230 amino acids in length, that is used for either homo- or hetero-oligomerization among the TRAF family to interact with the cytoplasmic regions of the TNFRs or for interactions with downstream signal transducers. Rothe et al., Proc. Natl. Acad. Sci. USA, 93:8241–8246 (1996); Song et al., Proc. Natl. Acad. Sci. USA, 93:6721–6725 (1996); Cheng et al., Genes Dev., 10:963–973 (1996). In addition to the TRAF domain, most of the TRAF family members contain an N-terminal RING finger and several zinc finger structures which appear to be important for their effector functions. Regnier et al., J. of Biol. Chem., 270:25715–25721 (1995); Hu et al., J. Biol. Chem., 269:30069–30072 (1994); Moisalos et al., Cell, 80: 389–399 (1995).

Several effector functions of TRAFs were revealed by recent experiments based on a transfection system. TRAF2, first identified by its interaction with TNFR2, was subsequently shown to mediate NF-kB activation induced by two TNF receptors, CD40 and CD30. Rothe et al., Science, 269:1424–1427 (1995); Lee et al., Proc. Natl. Acad. Sci. USA, 93: 9699–9703 (1996). TRAF5 was also implicated in NF-kB activation mediated by LT-bR, whereas TRAF3 (also known as CRAF1, CD40bp or LAP1) was shown to be involved in the regulation of CD40-mediated CD23 up-regulation in B cells. Cheng et al., Science, Id. Other TRAF members in the TNFR family-mediated signal transduction have potential effector functions as adapter proteins to recruit different downstream signal transducers to the receptor complex. For example, TRAF1 is required for the recruitment of members of the c-IAP (cellular Inhibitor of Aoptosis Protein) family to the TNFR2 signaling complex. Rothe et al., Cell, 83:1243–1252 (1995).

In addition to signal transduction with TNFR family members, TRAFs also have the potential to regulate other receptor-mediated signaling pathways. For example, TRAF6 is a component of interleukin-1 receptor (IL-1R) signaling complex in which it mediates the activation of NF-kB by IL-1R. Cao et al., Nature, 383:443–446 (1996). Since TRAFs form homo- or hetero-oligomers, it is suggested that the repertoire of TRAF members in a given cell type may differentially affect the intracellular signals triggered by these receptors. This may be accomplished by the selective interaction of TRAFs with a specific set of downstream signal transducers.

Although many aspects of TRAF-mediated effector functions leading to cellular activation have been defined, there is a need in the art for a determination as to whether TRAF proteins will also mediate the apoptotic signals induced by the death-domain-less members of the TNFR superfamily. Zheng et al., Nature, 377:348–351 (1995); Gruss et al., Blood, 83: 2045–2056 (1994); Amakawa et al., Cell, 84:551–562 (1996).

In view therefore, the present disclosure describes the isolation and characterization of a novel protein component that associates with the receptor-TRAF signaling complex and inhibits the TRAF2-mediated NF-kB activation, which can determine whether a given cell proliferates or dies.

SUMMARY OF THE INVENTION

In accordance with the present invention, a novel component of the receptor-TRAF signaling complex, designated TRIP (Tumor necrosis factor Receptor associated factor Interacting Protein) has been identified, characterized and disclosed uniquely herein. The TRIP structure contains a RING finger motif and an extended coiled-coil domain, and when associated with the TNFR2 or CD30 signaling complex through TRAF transducers, TRIP functions as an inhibitor of TRAF2-mediated NF-kB activation. Since TRAF2-mediated NF-kB activation is closely linked to prevention of cellular apoptosis, TRIP, its active fragments, its structural or functional analogs, and its agonists or antagonists, can all be used as receptor-proximal regulators for influencing signals responsible for cell activation/proliferation or cell death.

Stimulation of members of the TNFR superfamily activates signaling cascades leading to the regulation of a cell's activation, growth or death. Many of these signal transducers contain either TRAF or death domains, which mediate protein-protein interactions. The TRAF family proteins interact directly with some members of the TNFR family and play a role in the activation of signaling pathways induced by these receptors. Once associated with the receptors, these proteins recruit downstream signal molecules that act to initiate cascades leading to cell activation or death. The present invention includes the identification and characterization of a novel regulator proximal to the TNFR/TRAF signaling complex.

The structure of the TRIP includes an N-terminal RING finger motif followed by a long coiled-coil domain divided into two subdomains. Amino acid sequences of the N-terminal half of the coiled-coil domain of TRIP shows about 50% similarity to the rod-like, coiled-coil structure of the myosin heavy chain, while those of the C-terminal half of the coiled-coil domain are characteristic of a leucine-zipper.

The coiled-coil domain of TRIP is required, not only for TRIP-TRAF interactions, but also for the inhibition of TRAF2-mediated NF-KB activation by TRIP. The RING finger domain of TRIP plays a regulatory role based on analogy to other RING-finger proteins. The C-terminal half of TRIP distal to the coiled-coil domain does not show any significant homology to other proteins but contains several phosphorylation sites, suggesting kinase regulation of TRIP.

TRIP is recruited to the receptors, TNFR2 or CD30, via its interaction with TRAF proteins. The recruitment of TRIP to these receptors is efficient in the presence of the TRAF2 oligomer. TRIP also inhibits the induction of NF-kB activation mediated by TNFR1, which indirectly interacts with TRAF2 via TRADD (see page 2, supra). In transient transfection assays, TRIP inhibited NF-kB activation induced by TNFR2, CD30 and TNFR1, and also by TRADD, all of which activates NF-kB via TRAF2. However, TRIP did not inhibit the activation of NF-kB by IL-1R which is mediated by TRAF6, confirming that the negative effect of TRIP on NF-kB activation is specific to a TRAF2-mediated pathway.

The specificity demonstrated by TRIP makes it unique among other signal transducers such as I-TRAF and A20 which inhibit TRAF2-mediated NF-kB activation. In contrast to TRIP, both I-TRAF and A20 inhibit the activation of NF-kB induced by IL-1R as well as by TNFRs. TRIP differs from I-TRAF or A20 in several additional aspects. First, TRIP is recruited to the cognate receptor-TRAF signaling complex, while I-TRAF is not; and TRIP can be recruited to the cognate receptors via its interaction with TRAF2 homo-oligomer, while A20 interacts only with TRAF2-TRAF1 hetero-oligomer.

Second, the inhibitory mechanism acting on NF-kB activation by I-TRAF, A20 and TRIP appears to be different. I-TRAF inhibits TRAF2-mediated NF-kB activation by blocking the recruitment of TRAF2 to the receptor complex which would normally initiate the clustering of TRAF proteins. In contrast, TRIP is recruited to the receptor complex by its association with TRAF2. Although A20 interacts with TRAFs, its inhibitory effect on TRAF2-mediated NF-kB activation does not require direct protein-protein interaction in transfection assays. TRIP, however, inhibits TRAF2-mediated NF-kB activation only when its coiled-coil domain, required for the TRIP-TRAF interaction, is intact.

TRIP specificity is also demonstrated in contrast with the c-IAPs (see pages 3–4, supra). TRIP and the c-IAP's are the only two protein types which are recruited to the receptor-TRAF complex. In contrast to TRIP, however, c-IAPs do not exert a negative effect on the activation of NF-kB induced by receptors. In addition to their functional differences, TRIP and c-IAPs are recruited differently to their cognate receptors. TRIP can be recruited to the cognate receptors (TNFR2 or CD30) in the presence of TRAF2 homo-oligomer, while c-IAPs are recruited to TNFR2 only through TRAF2-TRAF1 hetero-oligomer.

As a receptor-proximal negative regulator of NF-kB activation, TRIP through signals mediated by the TNFR2- or CD30-TRAF signaling complex can initiate seemingly opposing effects on cells, namely cell activation/growth or cell death. The balance of pro-activation/growth or pro-cell death signals mediated by the receptor-TRAF complex are controlled by the particular set of signal transducers (i.e. c-IAPs or TRIP) which are recruited to the receptor complex. When c-IAPs are recruited to the receptor complex, TRAF2-mediated NF-kB activation proceeds unaffected. The activation of NF-kB induces the expression of various genes and also suppresses cell death which drives the cells towards the pro-activation/growth state. When TRIP is recruited to the receptor complex it inhibits NF-kB activation which is required for anti-apoptotic signals. In addition, the contributions of other anti-apoptotics such as manganese superoxide dismutase or A20 will be diminished. Thus, the particular signals from the receptor-TRAF-TRIP complex will drive cells toward the anti-activation, pro-cell death state.

TRIP is further characterized by its particular effects on lymphoctes. The choice of which type of signal transducer (c-IAPs or TRIP) is to be recruited to the cognate receptors is most likely determined by their availability and by the presence of different TRAF proteins such as TRAF1. The expression of TRAF1 is tissue-specific while that of TRAF2 is not, and when lymphocytes are stimulated to proliferate via their antigen receptors the expression of c-IAP1 or TRAF1 is upregulated while TRIP expression is decreased. Consistently, TRAF2 expression is not significantly affected during lymphocyte proliferation. During antigen-stimulation of lymphocytes, therefore, the formation of TRAF2-TRAF1-c-IAP complex will be favored and recruited to the cognate TNFR family members, which exerts co-stimulatory signals for lymphocyte proliferation. TRAF1 overexpression antagonizes the formation of TRAF2 homo-oligomer in cells, which inhibits the activation-induced cell death of mature $CD8^+$ T cells, normally mediated by the TNFR2 signaling complex. TRIP expression is also most abundant in thymocytes which are destined to die during clonal deletion which is in part mediated by CD30.

In one aspect, the present invention extends to a novel protein having the following characteristics:

1. A structure which contains an extended coiled-coil domain, in particular, a domain selected from the amino acid residue sequences numbered 56–275 shown in FIGS. 2A–2B (SEQ ID NO: 3) (SEQ ID NO: 4); and 2. which, when associated with the TNFR2 or CD30 signaling complex through TRAF transducers, functions as an inhibitor of TRAF2-mediated NF-kB activation.

In a further aspect, the invention comprises TRIP, in particular, TRIP having an amino acid sequence selected from the full-length sequences shown in FIGS. 2A–2B (SEQ ID NO: 1) (SEQ ID NO: 2), its active fragments, its structural or functional analogs, and its agonists or antagonists, which can all be used as receptor-proximal regulators for influencing signals responsible for cell activation/proliferation or cell death.

TRIP can be characterized as a novel regulator proximal to the TNFR/TRAF signaling complex which has in its protein structure (FIG. 2C):

1. an N-terminal RING finger motif, in particular, those having an amino acid sequence selected from the sequences shown in FIG. 2D, SEQ ID NO: 5 and SEQ ID NO: 6;

2. followed by a long coiled-coil domain divided into two subdomains, the first subdomain being similar to the myosin heavy chain domain, and the second C-terminal subdomain characterized by a leucine-zipper.

Functionally, TRIP is recruited to TNFR2 or CD30 receptors via interaction with TRAF proteins, specifically the TRAF2 homo-oligomer. TRIP inhibits the induction of NF-kB activation induced by TNFR2, CD30, TNFR1 and TRADD specifically through the TRAF2-mediated pathway. TRIP does not inhibit the activation of NF-kB by IL-1R which is mediated by TRAF6.

TRIP inhibits TRAF2-mediated NF-kB activation only when its coiled-coil domain, required for the TRIP-TRAF interaction, is intact. The inhibition via the receptor-TRAF-TRIP complex drives an effected cell toward the anti-activation, pro-cell death state. When lymphocytes are stimulated to proliferate via their antigen receptors, the expression of TRIP is decreased, while TRIP expression is abundant in thymocytes which are destined to die.

The present invention also relates to a recombinant DNA molecule or cloned gene, or a degenerate variant thereof, which encodes a nucleic acid molecule, in particular, a recombinant DNA molecule or cloned gene, which has a nucleotide sequence selected from the sequences shown in FIG. 8A (SEQ ID NO: 7) and FIG. 8B (SEQ ID NO: 8). According to other features of certain embodiments of the present invention, a recombinant expression system is provided to produce biologically active animal or human TRIP, its active fragments, and its structural or functional analogs.

The human and murine DNA sequences (SEQ ID NO: 7) (SEQ ID NO: 8) for TRIP or portions thereof, may be prepared as probes to screen for complementary sequences and genomic clones in the same or alternate species. The present invention extends to probes so prepared that may be provided for screening cDNA and genomic libraries for TRIP. The present invention also includes the preparation of plasmid vectors, and the use of the DNA sequences to construct vectors expressing antisense RNA or ribozymes which would attack the mRNAs of any or all of the DNA sequences set forth in FIG. 8A (SEQ ID NO: 7) and FIG. 8B (SEQ ID NO: 8). Correspondingly, the preparation of antisense RNA and ribozymes are included herein.

In a further embodiment of the invention, the full DNA sequence of the recombinant DNA molecule or cloned gene may be operatively linked to an expression control sequence which may be introduced into an appropriate host. The invention accordingly extends to unicellular hosts transformed with the cloned gene or recombinant DNA molecule comprising a DNA sequence encoding TRIP, and more particularly, the complete DNA sequences shown in FIG. 8A (SEQ ID NO: 7) and FIG. 8B (SEQ ID NO: 8).

The concept of the present invention contemplates that specific factors exist for correspondingly specific ligands, such as for the TNFR2, CD30, TNFR1 and TRADD and the like which have a specificity for the TRAF2-mediated pathway, as described earlier. Accordingly, this specificity and the direct involvement thereto by TRIP offers the promise of a broad spectrum of diagnostic and therapeutic utilities.

The present invention naturally contemplates several means for preparation of TRIP, its active fragments, and its structural or functional analogs, including known recombinant techniques, and the invention is accordingly intended to cover such synthetic preparations within its scope. The isolation of the cDNA (SEQ ID NO: 7) (SEQ ID NO: 8) and amino acid sequences disclosed herein facilitates their reproduction by such recombinant techniques, and accordingly, the invention extends to expression vectors prepared from the disclosed DNA sequences for expression in host systems by recombinant DNA techniques, and to the resulting transformed hosts.

According to other preferred features of certain preferred embodiments of the present invention, a recombinant expression system is provided to produce biologically active animal or human TRIP.

The invention includes an assay system for screening of potential drugs effective to modulate the activity of target mammalian cells by interrupting or potentiating the effects of TRIP, its active fragments, and its structural or functional analogs.

The assay system could be adapted to identify drugs or other entities that are capable of binding to TRIP, its active fragments or its structural/functional analogs, either in the cytoplasm or in the nucleus, thereby inhibiting or potentiating NF-kB activity. Such assay would be useful in the development of drugs that would be specific against particular cellular activity, or that would potentiate such activity, in time or in level of activity. For example, such drugs might be used to inhibit lymphocyte apoptosis thereby prolonging the cellular life of certain sub-populations of T cells.

In yet a further embodiment, the invention contemplates antagonists of the activity of TRIP. In particular, an agent or molecule which promotes TRAF2-mediated NF-kB activation. In a specific embodiment, the antagonist can be a peptide having a sequence complementary to the coiled-coil domains as shown by amino acid residues 56–275 shown in FIG. 2A.

The present invention also extends to the development of antibodies against TRIP, its active fragments, and its structural or functional analogs, including naturally raised and recombinantly prepared antibodies. For example, the antibodies could be used to screen expression libraries to obtain the gene or genes that encode for TRIP in other animal species. Or such anti-bodies could be used to diagnose for TRIP deficiency or overexpression in potential human patients.

Such antibodies could include both polyclonal and monoclonal antibodies prepared by known genetic techniques, as well as bi-specific (chimeric) antibodies, and antibodies including other functionalities suiting them for additional diagnostic use conjunctive with their capability of modulating TRIP activity.

Thus, TRIP, its active fragments, its structural or functional analogs, and any antagonists or antibodies that may be raised thereto, are capable of use in connection with various diagnostic techniques, including immunoassays, such as a radioimmunoassay, using for example, an antibody to the aforementioned proteins that has been labeled by either radioactive addition, or radioiodination.

In an immunoassay, a control quantity of antibodies to TRIP, or the like, may be prepared and labeled with an enzyme a specific binding partner and/or a radio-active element, and may then be introduced into a cellular sample. After the labeled material or its binding partner(s) has had an opportunity to react with sites within the sample, the resulting mass may be examined by known techniques, which may vary with the nature of the label attached.

In the instance where a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I and $^{186}$Re are used, known currently available counting procedures may be utilized. In the instance where the label is an enzyme, detection may be accomplished by any of the presently utilized colorimetric, spectrophotometric, fluorospectro-photometric, amperometric or gasometric techniques known in the art.

The present invention includes an assay system which may be prepared in the form of a test kit for the quantitative analysis of the extent of the presence of TRIP, its active fragments, its structural or functional analogs, or to identify drugs or other agents that may mimic or block their activity. The system or test kit may comprise a labeled component prepared by one of the radioactive and/or enzymatic techniques discussed herein which couples a label to a binding partner for TRIP such as an anti-TRIP antibody, and one or more additional immunochemical reagents.

In a further embodiment, the present invention relates to certain therapeutic methods which would be based upon the activity of TRIP, its subunits, or active fragments thereof, or upon agents or other drugs determined to possess the same activity. A first therapeutic method is associated with the prevention of the manifestations of conditions causally related to or following from the binding activity of TRIP or its subunits, and comprises administering an agent capable of modulating the production and/or activity of TRIP or subunits thereof, either individually or in mixture with each other in an amount effective to prevent the development of those conditions in the host. For example, drugs or other binding partners to TRIP may be administered to inhibit or potentiate NF-kB activity.

More specifically, the therapeutic method generally referred to herein could include the method for the treatment of various pathologies or other cellular dysfunctions and derangements by the administration of pharmaceutical compositions that may comprise effective inhibitors or enhancers of activation of TRIP or its subunits, or other equally effective drugs developed for instance by a drug screening assay prepared and used in accordance with a further aspect of the present invention. For example, drugs or other binding partners to TRIP or proteins as represented by SEQ ID NOS: 1–6, may be administered to inhibit or potentiate TRIP activity.

Accordingly, it is a principal object of the present invention to provide the TRIP protein and its subunits in purified form that exhibits certain characteristics and activities associated with cell growth, activation, proliferation and apoptosis.

It is a further object of the present invention to provide antibodies to the TRIP and its subunits, and methods for their preparation, including recombinant means.

It is a further object of the present invention to provide a method for detecting the presence of TRIP and its subunits in mammals in which invasive, spontaneous, or idiopathic pathological states are suspected to be present.

It is a further object of the present invention to provide a method and associated assay system for screening substances such as drugs, agents and the like, potentially effective in either mimicking the activity or combating the adverse effects of the TRIP and/or its subunits in mammals.

It is a still further object of the present invention to provide a method for the treatment of mammals to control the amount or activity of TRIP or subunits thereof, so as to alter the adverse consequences of such presence or activity, or where beneficial, to enhance such activity.

It is a still further object of the present invention to provide a method for the treatment of mammals to control the amount or activity of TRIP or its subunits, so as to treat or avert the adverse consequences of invasive, spontaneous or idiopathic pathological states.

It is a still further object of the present invention to provide pharmaceutical compositions for use in therapeutic methods which comprise or are based upon the TRIP, its subunits, their binding partner(s), or upon agents or drugs that control the production, or that mimic or antagonize the activities of the TRIP.

Yet a further object is to provide a test kit for the quantitative analysis of the extent of the presence of TRIP, its active fragments, its structural or functional analogs, or to identify drugs or other agents that may mimic or block their activity.

Other objects and advantages will become apparent to those skilled in the art from a review of the ensuing description which proceeds with reference to the following illustrative drawings.

BRIEF DESCRIPTION OF THE DRAWINGS

FIGS. 2A–2B depicts the amino acid sequences of human TRIP (hTRIP) (SEQ ID NO: 1) and mouse TRIP (mTRIP) (SEQ ID NO: 2).

FIG. 2D is a comparison chart of amino acid sequences of the RING finger domains of hTRIP (SEQ ID NO: 5), mTRIP (SEQ ID NO: 6), mTRAF2 (SEQ ID NO: 9), mTRAF3 (SEQ ID NO: 10) mc-IAP1 (SEQ ID NO: 11), human proto-oncogene c-cbl (SEQ ID NO: 12), human RING1 (SEQ ID NO: 13), human ribonucleoprotein SS-A/Ro (SEQ ID NO: 14), chicken C-RZF (SEQ ID NO: 15), and Drosophila neuralized gene, neu (SEQ ID NO: 16).

FIG. 8A and FIG. 8B depict the cDNA sequences for human and mouse TRIP (SEQ ID NO: 7) (SEQ ID NO: 8), respectively.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994))]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

If appearing herein, the following terms shall have the definitions set out below. The terms active fragments, structural analogs, functional analogs or mimics, as used in conjunction with the term TRIP, and any variants not specifically listed, may be used herein interchangeably, and as used throughout the present application and claims refer to proteinaceous material including single or multiple proteins, and extends to those proteins having the amino acid sequence data described herein and presented in FIGS. 2A–2B, SEQ ID NO: 1, SEQ ID NO: 2, SEQ ID NO: 3 and SEQ ID NO: 4, and FIG. 2D, SEQ ID NO: 5 and SEQ ID NO: 6, and the profile of activities set forth herein and in the Claims. Accordingly, proteins displaying substantially equivalent or altered activity are like-wise contemplated. These modifications may be deliberate, for example, such as modifications obtained through site-directed mutagenesis, or may be accidental, such as those obtained through mutations in hosts that are producers of the complex or its named subunits. Also, the term TRIP is intended to include within its scope proteins specifically recited herein as well as all homologous analogs and allelic variations.

Figure 2A:
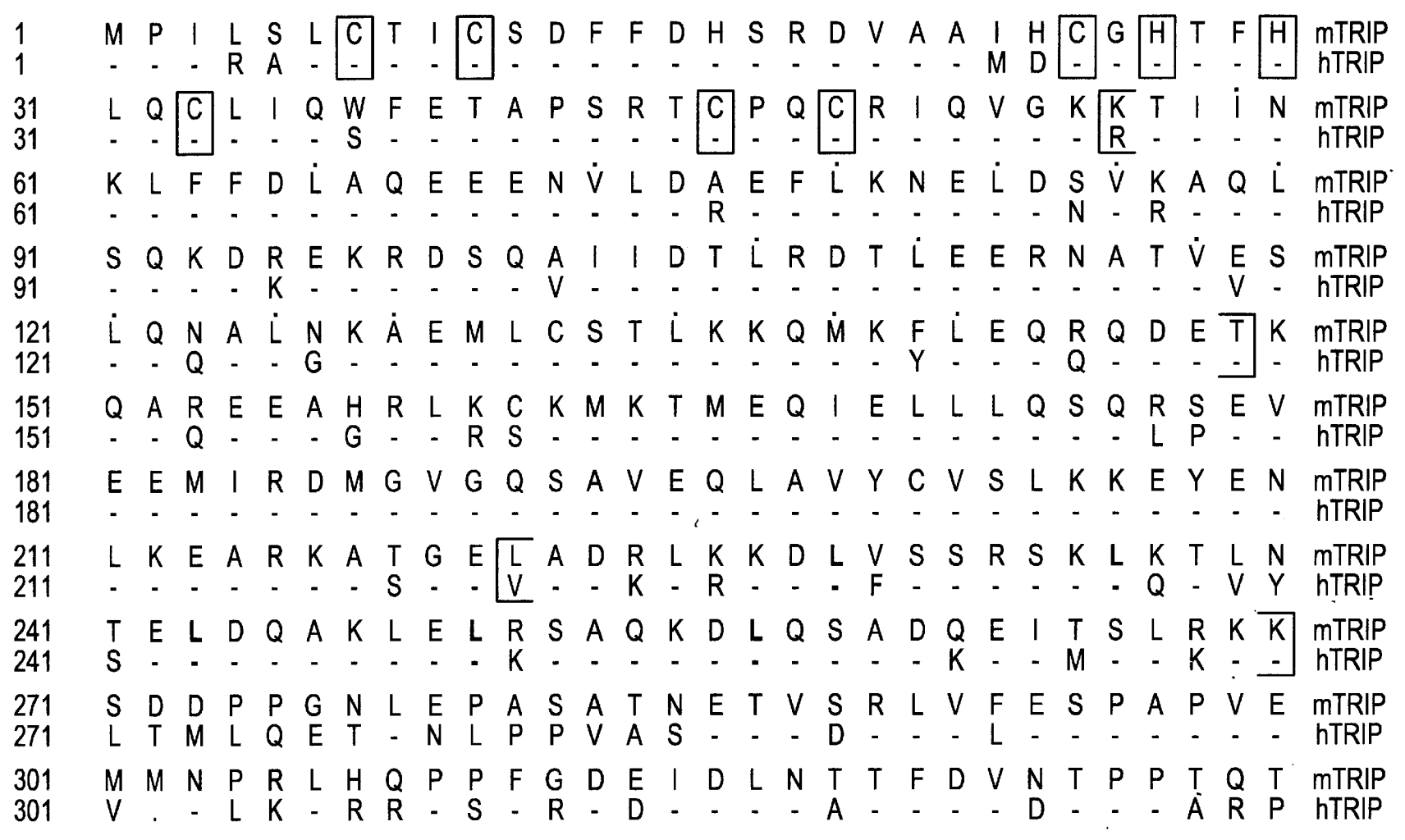
Figure 2B:
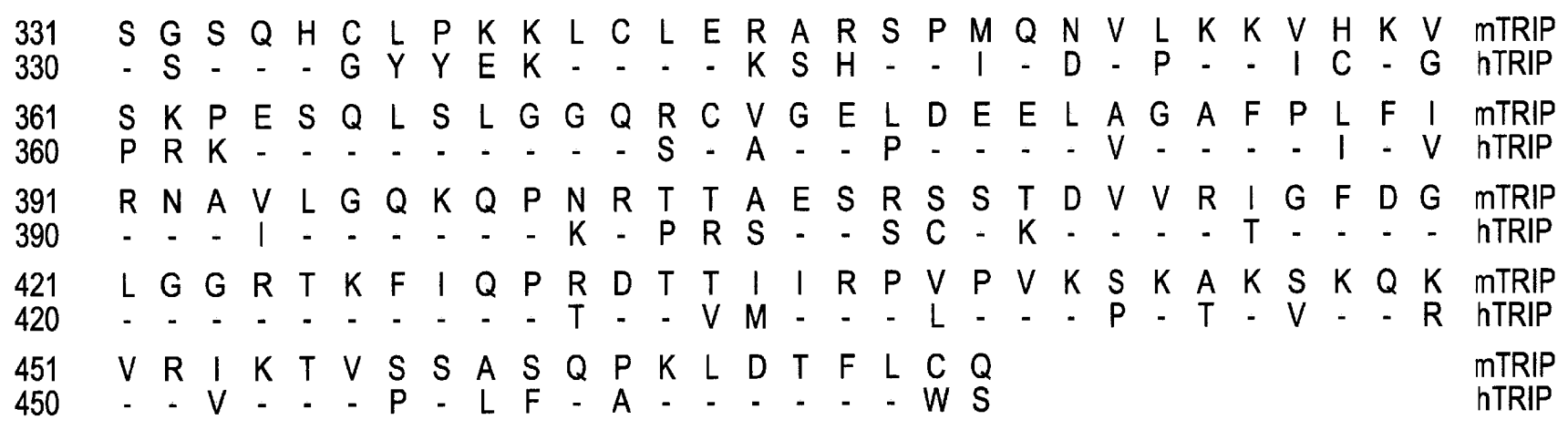
Figure 2C:
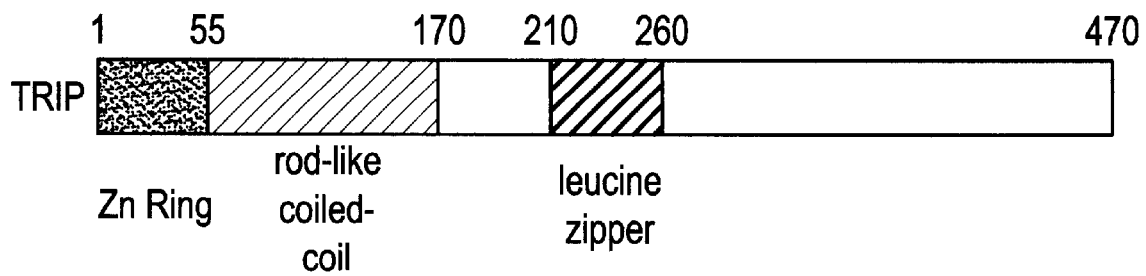
FIG. 2C depicts the protein structure of TRIP, having an N-terminal RING finger motif; and a long coiled-coil domain comprising a C-terminal subdomain characterized by a leucine-zipper.

The terms agonists or antagonists when used in conjunction with the term TRIP, and in addition to their ordinary meanings to one skilled in the art, refer to proteinaceous or non-proteinaceous materials, including inorganic or organic combinations of elements, compounds, compositions or peptidomimetics which function positively or negatively, inhibit, up- or down-regulate functions similar to that produced by the amino acid sequence or fragments thereof as described herein and presented in FIGS. 2A–2B, SEQ ID NO: 1, SEQ ID NO: 2, SEQ ID NO: 3 and SEQ ID NO: 4, and FIG. 2D, SEQ ID NO: 5 and SEQ ID NO: 6, and the profile of activities set forth herein and in the Claims.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10–20° C. below the predicted or determined $T_m$ with washes of higher stringency, if desired.

The amino acid residues described herein are preferred to be in the "L" isomeric form. However, residues in the "D" isomeric form can be substituted for any L-amino acid residue as long as the desired fuctional properties is retained by the polypeptide. In keeping with standard polypeptide nomenclature, abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. The above Table is presented to correlate the three-letter and one-letter notations which may appear alternately herein and especially in the FIGURES.

The phrase "pharmaceutically acceptable" refers to molecular entities and compositions that are physiologically tolerable and which do not typically produce an allergic or similar undesired hyper/hypo-reaction when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, abnormal lymphocyte counts, morphology, differentiation or distribution.

As stated above, the present invention also relates to a recombinant DNA molecule or cloned gene, or a degenerate variant thereof, which encodes the full length sequences shown in FIGS. 2A–2B (SEQ ID NO: 1) (SEQ ID NO: 2), or a fragment thereof; preferably a nucleic acid molecule, in particular a recombinant DNA molecule or cloned gene, encoding the nucleotide sequences shown in FIG. 8A (SEQ ID NO: 7) and FIG. 8B (SEQ ID NO: 8).

The possibilities both diagnostic and therapeutic that are raised by the existence of the TRIP, derive from the fact that the factors appear to participate in direct and causal protein-protein interaction between the TNFR2 or CD30 receptors via interaction with TRAF proteins, specifically the TRAF2 homo-oligomer. As suggested earlier and elaborated further on herein, the present invention contemplates pharmaceutical intervention in the cascade of reactions in which the TRIP is implicated, to modulate the activity initiated by the induction of NF-kB activation by TNFR2, CD30, TNFR1 and TRADD specifically through the TRAF2-mediated pathway.

Thus, in instances where it is desired to reduce or inhibit the induction of NF-kB activation resulting from a particular stimulus or factor, an appropriate inhibitor of TRIP could be introduced to block the TRAF2-mediated pathway. Correspondingly, in situations where insufficient TRIP activity is taking place, the remedy could be through the introduction of additional quantities of potentiators of TRIP expression, potentiators of expression of TRIP analogs, fragments and the like, or chemicals or pharmaceutical cognates which enhance TRIP expression or function equivalently to TRIP.

As discussed earlier, binding partners to TRIP or proteins as represented by SEQ ID NOS: 1–6, or other ligands or agents exhibiting either mimicry or antagonism to the TRIP activity or control over their production, may be prepared with a suitable carrier and at a strength effective for administration by various means to a patient experiencing an adverse medical condition associated with specific deficiency or excess in TRIP or its activity for the treatment thereof.

A variety of administrative techniques may be utilized, among them parenteral techniques such as subcutaneous, intravenous and intraperitoneal injections, catheterizations and the like. Average quantities of TRIP or their subunits may vary and in particular should be based upon the recommendations and prescription of a qualified physician or veterinarian.

Also, antibodies including both polyclonal and monoclonal antibodies, and drugs that modulate the production or activity of TRIP and/or their subunits may possess certain diagnostic applications and may for example, be utilized for the purpose of detecting and/or measuring conditions which demonstrate abnormal TRIP activity. For example, TRIP or its subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of TRIP may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against TRIP can be screened for various properties; i.e., isotype, epitope, affinity, etc. Of particular interest are monoclonal antibodies that neutralize the activity of TRIP or its subunits. Such monoclonals can be readily identified in TRIP activity assays.

Preferably, the anti-TRIP antibody used in the diagnostic methods of this invention is an affinity purified polyclonal antibody. More preferably, the antibody is a monoclonal antibody (mAb). In addition, it is preferable for the anti-TRIP antibody molecules used herein be in the form of Fab, Fab', F(ab')$_2$ or F(v) portions of whole antibody molecules.

As suggested earlier, the diagnostic method of the present invention comprises examining a cellular sample or medium by means of an assay including an effective amount of an antagonist to TRIP, such as an anti-TRIP antibody, preferably an affinity-purified polyclonal antibody, and more preferably a mAb. It is preferable for the anti-TRIP antibody molecules used herein be in the form of Fab, Fab', F(ab')$_2$ or F(v) portions or whole antibody molecules.

Methods for producing polyclonal anti-polypeptide antibodies are well-known in the art. See for example U.S. Pat. No. 4,493,795 to Nestor et al. A monoclonal antibody, typically containing Fab and/or F(ab')$_2$ portions of useful antibody molecules, can be prepared using the hybridoma technology described in *Antibodies—A Laboratory Manual,* Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with TRIP, a TRIP-binding portion thereof, or an origin-specific DNA-binding portion thereof.

Splenocytes are typically fused with myeloma cells using polyethylene glycol (PEG) 6000. Hybridomas producing a monoclonal antibody useful in practicing this invention are identified by their ability to immunoreact with the present TRIP and their ability to inhibit specified TRIP activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

Methods for producing monoclonal anti-TRIP antibodies are also well-known in the art. See Niman et al., *Proc. Natl. Acad. Sci. USA*, 80:4949–4953 (1983). Typically, the present TRIP or a protein analog is used either alone or conjugated to an immunogenic carrier. The hybridomas are screened for the ability to produce an antibody that immunoreacts with the TRIP or protein analog.

The present invention further contemplates therapeutic compositions useful in practicing the therapeutic methods of this invention. A subject therapeutic composition includes, in admixture, a pharmaceutically acceptable excipient (carrier) and one or more of TRIP, a protein analog thereof or fragment thereof, as described herein as an active ingredient. In a preferred embodiment, the composition comprises an antigen capable of modulating the specific binding of the present TRIP within a target cell.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic compositions are conventionally administered intravenously, for example, by injection of a unit dose. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of TRIP binding capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMB9 and their derivatives, plasmids such as RP4; phage DNAS, e.g., the numerous phage derivatives, e.g., NM989, and other phage DNA, e.g., M13 and filamentous single stranded phage DNA; yeast plasmids such as the $2\mu$ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the control regions of fd coat protein, the promoter for 3-phosphoglycerate kinase or other glycolytic enzymes, the promoters of acid phosphatase (e.g., PhoS), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli,* Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that TRIP analogs may be prepared from nucleotide sequences of the protein complex/subunit derived within the scope of the present invention. Analogs, such as fragments, may be produced, for example, by pepsin digestion of TRIP material. Other analogs, such as muteins, can be produced by standard site-directed mutagenesis of TRIP coding sequences. Analogs exhibiting "TRIP activity" such as small molecules, whether functioning as promoters or inhibitors, may be identified by known in vivo and/or in vitro assays.

As mentioned above, a DNA sequence encoding TRIP can be prepared synthetically rather than cloned. The DNA sequence can be designed with the appropriate codons for the TRIP amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, Nature, 292:756 (1981); Nambair et al., Science, 223:1299 (1984); Jay et al., J. Biol. Chem., 259:6311 (1984).

Synthetic DNA sequences allow convenient construction of genes which will express TRIP analogs or "muteins". Alternatively, DNA encoding muteins can be made by site-directed mutagenesis of native TRIP genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, Science, 244:182–188 (April 1989). This method may be used to create analogs with unnatural amino acids.

The present invention extends to the preparation of antisense oligonucleotides and ribozymes that may be used to interfere with the expression of the TRIP at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into TRIP-producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, molecules can be engineered so that they recognize specific nucleotide sequences in an RNA molecule and cleave it. Because they are sequence-specific, only mRNAs with particular sequences are inactivated.

Investigators have identified two types of ribozymes, Tetrahymena-type and "hammerhead"-type. (Hasselhoff and Gerlach, 1988) Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences described herein may thus be used to prepare antisense molecules against, and ribozymes that cleave mRNAs for TRIP and their ligands.

The present invention also relates to a variety of diagnostic applications, including methods for detecting the presence of stimuli such as the earlier referenced polypeptide ligands, by reference to their ability to elicit the activities which are mediated by the present TRIP. As stated earlier, TRIP can be used to produce antibodies to itself by a variety of known techniques, and such antibodies could then be isolated and utilized as in tests for the presence of particular TRIP activity in suspect target cells.

As described in detail above, antibody(ies) to TRIP can be produced and isolated by standard methods including the well known hybridoma techniques. For convenience, the antibodies to hTRIP will be referred to herein as $Ab_1$ and antibodies raised in another species as $Ab_2$.

The presence of TRIP in cells can be ascertained by the usual immunological procedures applicable to such determinations. A number of useful procedures are known. Three such procedures which are especially useful utilize antibody $Ab_1$ labeled with a detectable label, antibody $Ab_2$ labeled with a detectable label, or a combination of antibodies $Ab_1$ and $Ab_2$ each labeled with a detectable label. The procedures may be summarized by the following equations wherein the asterisk indicates that the particle is labeled, wherein, for example, $Ab_1$ is anti-hTRIP and $Ab_2$ is anti-TRIP of a non-human specie:

A. $TRIP+Ab_1^*=TRIPAb_1^*$

B. $TRIP+Ab_2^*=TRIPAb_2^*$

C. $TRIP+Ab_1+Ab_2^*=TRIPAb_1Ab_2^*$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody," or "DASP" procedure.

In each instance, TRIP forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another mammalian species as an antigen to raise the antibody $Ab_2$. For purposes of this description and Claims, $Ab_1$ will be referred to as a primary or anti-hTRIP antibody, and $Ab_2$ will be referred to as a secondary or anti-$Ab_1$ antibody which can include anti-mTRIP.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

Binding partner(s) for TRIP can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$ and $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

In a further embodiment of this invention, commercial test kits suitable for use by a medical specialist may be prepared to determine the presence or absence of predetermined TRIP activity or predetermined TRIP activity-capability in suspected target cells. In accordance with the testing techniques discussed above, one class of such kits will contain at least one labeled anti-TRIP antibody or another suitable binding partner, for instance an antibody specific to fragments of TRIP, and directions for use depending upon the method selected, e.g., "competitive," "sandwich," "DASP" and the like. The kits may also contain peripheral reagents such as buffers, stabilizers and the like for enhancing storage and durable use.

Accordingly, a test kit may be prepared for the demonstration of the presence or capability of cells for predetermined TRIP activity, comprising:

(a) a predetermined amount of at least one immunochemically reactive component obtained by direct or indirect contact with TRIP or any fragments or subunits of a full sequence selected from those shown in FIG. 2A (SEQ ID NO: 1) (SEQ ID NO: 2) or a binding partner thereto, and attaching a detectable label to the component;

(b) other reagents; and (c) directions for use of said kit.

In a further variation, the test kit may be prepared and used for the purposes stated above, which operates according to a predetermined protocol (e.g. "competitive," "sandwich," "double antibody," etc.), and comprises:

(a) a labeled component which has been obtained by coupling a anti-TRIP antibody to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between TRIP and anti-TRIP antibody and the various specific ligand interactions.

PRELIMINARY CONSIDERATIONS

The following examples are presented in order to more fully illustrate the preferred embodiments of the invention. They should in no way be construed, however, as limiting the broad scope of the invention.

EXAMPLE 1

Isolation of TRIP as a TRAF-Interacting Protein

In this example the yeast two-hybrid system was used to isolate TRIP taking advantage of its role as a TRAF1-interacting protein. By screening cDNA libraries derived from mouse thymocytes, multiple cDNA clones representing several distinct proteins were isolated. Among these, was one set of cDNA-encoded proteins which interacted with both TRAF1 and TRAF2 in the two-hybrid assay which was conducted as follows.

A bait plasmid pEG202-TRAF1 [Lee et al., *J. Exp. Med.* 183:669–674 (1996)] which encodes the LexA-DNA binding domain fused to TRAF1, was used for a yeast two-hybrid screening of a mouse thymocyte cDNA library. The isolation of positive clones and subsequent analyses were carried out as described in Lee et al., *J. Exp. Med.*, Id. The interaction of proteins in the two-hybrid assay was scored by the b-galactosidase activity of yeast transformants containing both activators and baits upon galactose induction as described in Lee et al., *Proc. Natl. Acad. Sci. USA*, 93:9699–9703 (1996).

In brief, yeast cells were permeabilized with 0.0025% SDS and 5% chloroform, and the cell debris was removed by centrifugation. The b-galactosidase assay was performed at 25° C. and OD420 was measured. The TRIP cDNA insert of approximately 1.0 kb isolated by two-hybrid screening was used as a probe to screen mouse thymocytes and T cell hybridoma cDNA libraries in lambda-ZAP (Strategene) as described in Park et al., *Immunity*, 4:583–591 (1996). A human thymocyte cDNA library in lambda-gt10 (Clontech) was similarly screened using full-length mTRIP cDNA. For sequence analysis of mTRIP and hTRIP, several overlapping cDNA clones were sequenced using the Sequenase Kit (United States Biochemical Co., Cleveland, Ohio). Northern analysis of mouse tissue RNA was performed as described in Park et al., *Immunity*, Id.

Analysis of the DNA sequence of the TRAF1- and TRAF2-interacting cDNA clones revealed that they are derived from a single novel gene named herein as TRIP. Since TRIP interacted strongly with both TRAF1 and TRAF2 in the two hybrid-assay, these proteins were tested for interaction in mammalian cells in the next example.

EXAMPLE 2

Cell Transfection Assay

In this example, expression vectors encoding TRAF1 or TRAF2 were coexpressed in 293 cells in the presence of an expression vector encoding either GST alone or GST-TRIP fusion protein.

Rabbit polyclonal antisera recognizing mTRIP were prepared by Animal Pharm Services, Inc. using bacteria-produced GST-TRIP fusion proteins. Polyclonal antisera were negatively selected with purified GST proteins before use. Anti-TRAF1 and anti-TRAF2 Abs were from Santa Cruz Biotechnology. The monoclonal Ab against the HA epitope (12CA5) was from BabCo. Recombinant human TNF and IL-1 were from R & D Systems.

Eukaryotic expression vectors for wild type or mutant forms of TRAF1 and TRAF2, CD8-TNFR2, CD8-CD30, GST-TNFR2, and GST-CD30 are described in Lee et al., *J. Exp. Med.*, Id. and *Proc. Natl. Acad. Sci. USA*, Id. Expression vectors for TRADD was made by cloning the PCR-amplified murine TRADD cDNA into to pHbApr-1-neo. To generate eukaryotic expression vectors for GST-wild type TRIP or mutant TRIPS, various TRIP cDNAs were generated by PCR and in-frame cloned into 5'-BamHI-NotI-3' sites in pEBG vector as described in Lee et al., *J. Exp. Med.*, Id.

Transfection of 293 cells were performed in 6 cm dishes by calcium phosphate precipitation as described in Lee et al., *J. Exp. Med.*, Id. Each transfection maintained an equal amount of total DNA by adding appropriate amount of the control vector, pcDNA3.1 (Invitrogen). Forty-eight hours after transfection, luciferase activity was determined and normalized relative to b-galactosidase activity.

Cell lysates were precipitated with glutathione-Sepharose beads, and analyzed by Western blot analysis with anti-TRAF1 or anti-TRAF2 antibodies. The 293 cells were transfected with various combinations of expression vectors and thirty-six hours after transfection, cells were harvested in phosphate-buffered saline/1 mM phenylmethylsulfonyl fluoride, pelleted, and lysed in lysis buffer (20 mM Hepes (pH 7.9), 100 mM KCl, 300 mM NaCl, 10 mM EDTA, 0.1% NP-40, plus protease inhibitors). After lysis, aliquots of cell lysates were incubated with glutathione-Sepharose (Pharmacia) for 2 hr at 4° C. The beads were then washed 5 times with the lysis buffer, followed by an additional wash with the lysis buffer lacking NP-40. The proteins were then recovered by boiling in SDS-PAGE sample buffer. The eluted proteins were separated on 10% SDS-PAGE and transferred to Immobilon P (Millipore). The blot was subjected to Western analysis using enhanced chemoluminoscence (ECL) system (Amersham).

Figure 1:
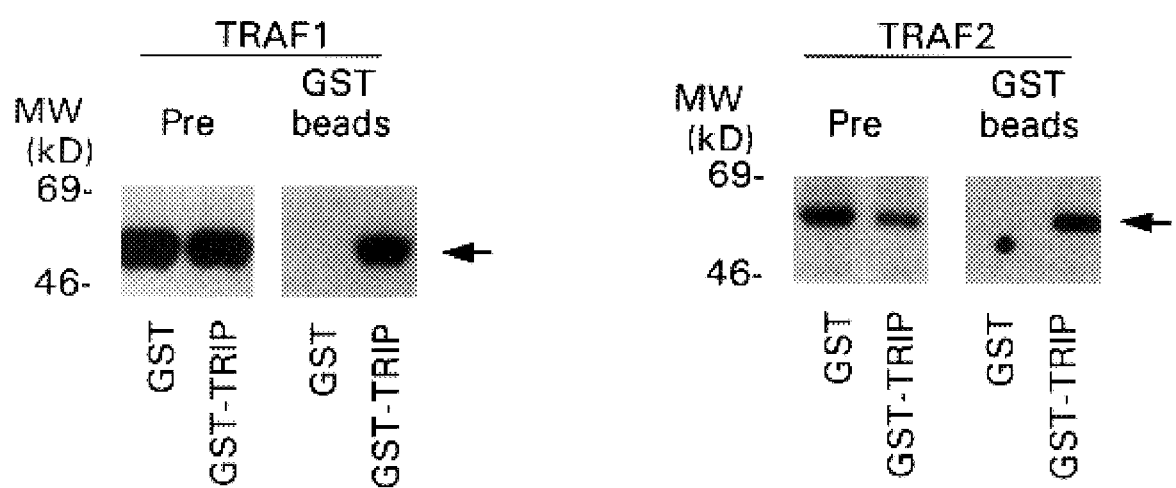
FIG. 1 shows the results of Western blot analysis of TRIP interactions with TRAF1 or TRAF2, using anti-TRAF1 and anti-TRAF2 polyclonal antibodies.

Consistent with the yeast two-hybrid assay, GST-TRIP coprecipitated both TRAF1 and TRAF2, demonstrating that TRIP can interact directly with TRAF1 and TRAF2 in human cells. FIG. 1 depicts the results of Western blot analysis. Cell lysates before precipitation with glutathione beads were analyzed by Western analysis to show that similar amounts of TRAF1 or TRAF2 are present in each sample. Proteins coprecipitated with GST-fusion proteins were analyzed. TRAF1 or TRAF2 are indicated with arrows.

Full-length sequence of TRIP was derived from sequence analysis of multiple cDNA clones from both thymocyte and T cell cDNA libraries. FIGS. 2A–2B show the full length mouse sequence (SEQ ID NO: 2), and the human sequence (SEQ ID NO: 1) is shown with one less amino acid, indicated with a dot at position 302. Dashes indicate positions in the human sequence which are identical to those in the mouse. Cysteine and histidine residues defining the RING finger motif are marked by boxes. Brackets indicate the coiled-coil regions of TRIP with the entire domain comprising residues 56–275 for both human (SEQ ID NO: 3) and mouse (SEQ ID NO: 4) TRIP. Within the brackets, amino acids that form the coiled-coil structures are marked by overlying dots, and those that form leucine-zipper structures are indicated in bold.

TRIP mRNA is predicted to encode proteins of 470 amino acids. Human TRIP encodes a 469 a.a. protein that is overall 76% identical to murine TRIP as shown in FIGS. 2A–2B. The amino acid sequence identity between the N-terminal half of mTRIP and hTRIP (residues 1–270) is even higher (87% identical). A homology search of the TRIP amino acid sequence revealed that TRIP is a novel protein with an N-terminal RING finger sequence motif.

FIG. 2D shows a comparison of amino acid sequences from various proteins that contain RING finger motifs. The RING finger domains of hTRIP (SEQ ID NO: 5), mTRIP (SEQ ID NO: 6), mTRAF2 (SEQ ID NO: 9), mTRAF3 (SEQ ID NO: 10), mc-IAP1 (SEQ ID NO: 11), human proto-oncogene c-cbl (SEQ ID NO: 12), human RING1 (SEQ ID NO: 13), human ribonucleoprotein SS-A/Ro (SEQ ID NO: 14), chicken C-RZF (SEQ ID NO: 15), and Drosophila neuralized gene, neu (SEQ ID NO: 16) are all shown with residues corresponding to the consensus sequence indicated in bold.

The N-terminal RING finger motif of TRIP is followed by an extended coiled-coil domain (SEQ ID NO: 3) (SEQ ID NO: 4). The coiled-coil domain of TRIP can be further divided into the N-terminal coiled-coil structure similar to the rod-like tails of myosin heavy chains (residues 56–150) [McLachlan et al., *Nature*, 299:226–231 (1982)], and the C-terminal leucine zipper-like coils (residues 221–260) [Landschulz et al., *Science*, 240:1759–1764 (1988)], both of which are implicated in protein-protein interactions.

Figure 2E:
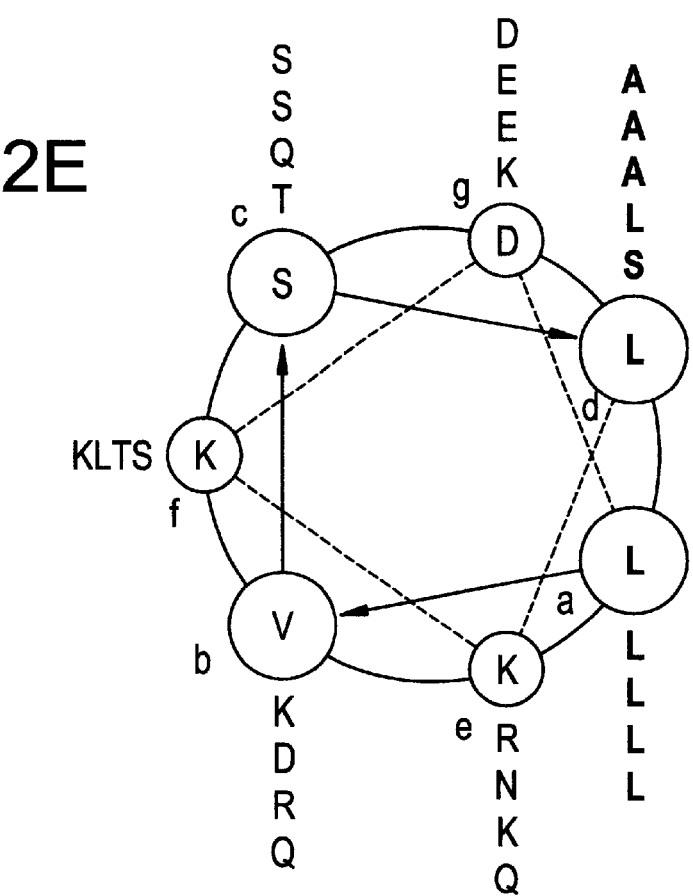
FIG. 2E is a helical wheel representation of TRIP residues beginning with inner residue Leu$^{225}$ at position d and finishing with the outer residue Ala$^{260}$ at position d.

FIG. 2E is a helical wheel representation of TRIP residues beginning with inner residue $Leu^{225}$ at position d and finishing with the outer residue $Ala^{260}$ at position d. The helical representation of the putative leucine zipper shows that the position next to the zipper is always hydro-phobic or uncharged, whereas other sides of the wheel contain charged but few hydrophobic residues, suggesting an amphipathic structure that can interact with another helix.

EXAMPLE 3

Expression Pattern Assay

Figure 3A:
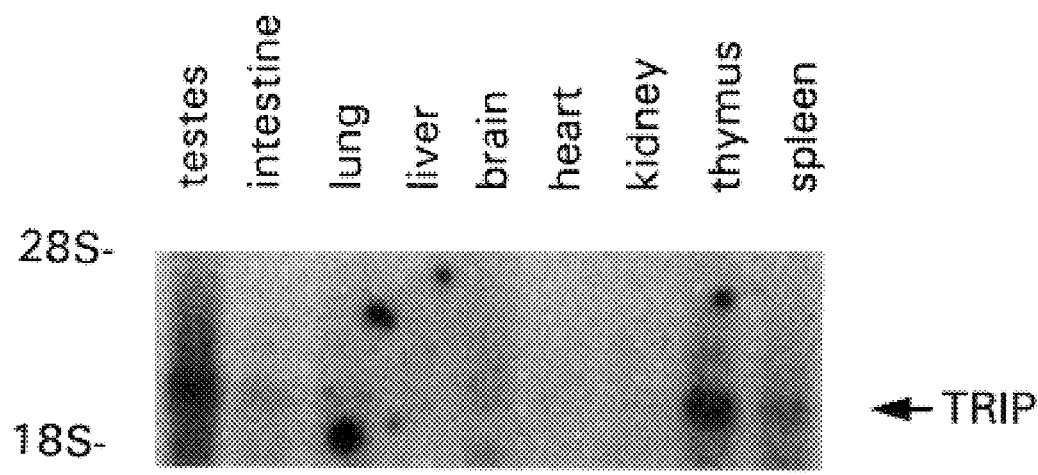
FIG. 3A shows the results of Northern blot analysis of TRIP mRNA in mouse tissues.

To characterize TRIP further, its expression pattern was examined. Northern blot analysis of various mouse tissue RNA samples revealed that TRIP-specific probes detected a ~2.1 kb mRNA species present in various tissues, but most abundant in testes, thymus and spleen. FIG. 3A shows the results of a Northern analysis of TRIP mRNA in mouse tissues. Total RNA isolated from various tissues was hybridized with TRIP-specific probe. The TRIP-probe hybridized to an approximately 2.1 kb mRNA, indicated by the arrow. Positions of 18S and 28S ribosomal RNA are indicated. The amount of total RNA loaded in each lane was similar based on the intensity of EtBr-stained rRNAs.

EXAMPLE 4

Expression Pattern in Lymphocytes

To characterize further the expression of TRIP in lymphocytes, its expression during lymphocyte proliferation by semi-quantitative PCR was analyzed. For the stimulation of lymphocytes, lymph node cells (LNC) were isolated from Balb/c mice (4–6 weeks old) and cultured on plates coated with anti-TCR Ab (10 ug/ml) and anti-CD28 Ab (1 ug/ml) for forty-eight hours as described in Park et al., *Immunity*, Id. Total RNA was prepared from unstimulated and stimulated LNCs using the Total RNA Isolation kit (Strategene). First-strand cDNA was synthesized from 10 mg of total RNA using M-MLV reverse transcriptase and random hexanucleotides following the protocols provided by the supplier (GIBCO BRL).

Quantitative PCR was performed in the linear phase of amplification by testing PCR products from different dilutions of first-strand cDNA products. PCR amplification was performed for 35 cycles using 1 of 1000 of the first-strand cDNA synthesized above. PCR products were then electrophoresed in a 2% agarose gel and subjected to Southern blot analysis.

Figure 3B:
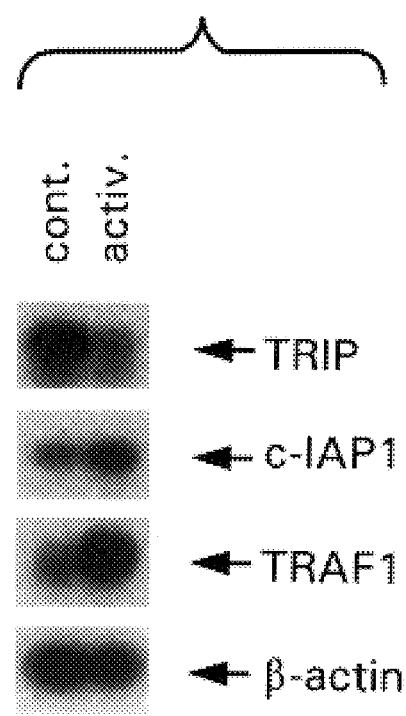
FIG. 3B depicts the expression of TRAF, c-IAP1 and TRIP during lymphocyte stimulation.

FIG. 3B shows the results of expression of TRAF, c-IAP1 and TRIP during lymphocyte stimulation. As noted above, the cDNAs were prepared from lymph node cells stimulated with anti-TCR Ab plus anti-CD28 Abs for 0 hr (cont.) and 48 hr (activ.). The cDNAs were then subjected to semi-quantitative PCR using primers specific for mTRIP, mTRAF1, and m-c-IAP1 as described above. The expression of TRIP was significantly reduced when lymphocytes were stimulated to proliferate via antigen receptors. This is in contrast to that of other components of the TNFR-TRAF signaling complex. For example, the expression of TRAF1 and c-IAP1 was upregulated upon lymphocyte proliferation. These results suggest that the repertoire of signal transducers available in a given cell type can change depending on the state of the cell.

Figure 4A:
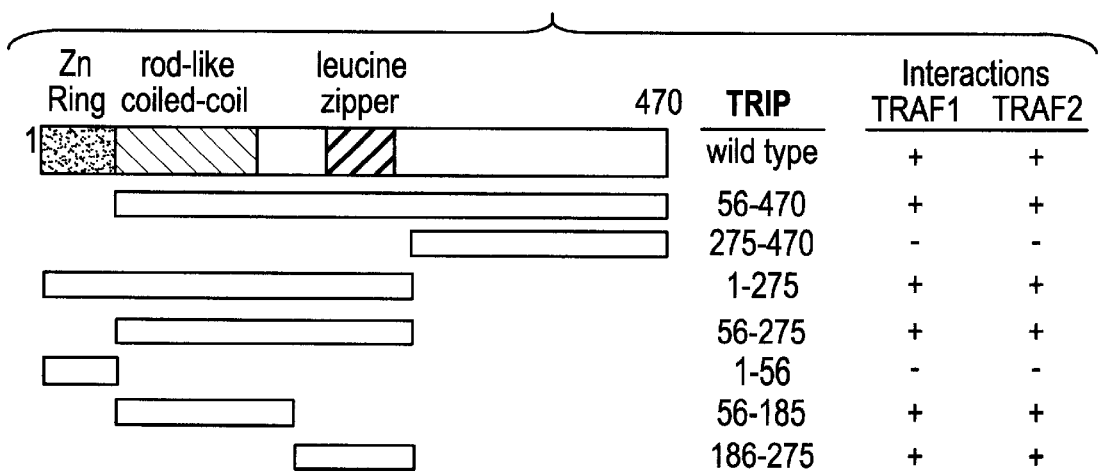
FIG. 4A is a map showing the interaction of TRAF1 or TRAF2 with the N- and C-terminal domains of TRIP.

The yeast two-hybrid assay was used to determine the structural requirements for the interaction of TRIP with TRAF1 or TRAF2. In the yeast two-hybrid assay, a mutant TRIP comprising the N-terminal half of the protein (residues 1–275 in FIGS. 2A–2B) interacted with TRAFs whereas a mutant TRIP lacking the N-terminal RING finger and the coiled-coil domain (residues 275–470 in FIGS. 2A–2B) failed to interact with the TRAFs. FIG. 4A shows the interaction of TRAF1 or TRAF2 with the N- and C-terminal domains of TRIP. Expression vectors encoding wild type TRIP or the indicated deletion mutants of TRIP fused to the transcription activation domain were cotransformed into yeast with plasmids expressing LexA DNA binding domain -TRAF1 or -TRAF2 fusion proteins. Interactions between fusion proteins were scored by measuring b-gal activity of yeast transformants. The "+" indicates average b-gal activity of three independent yeast transformants was higher than 1000 Miller units; and the "–" indicates average b-gal activity of three independent yeast transformants was about 100 Miller units, which was similar to that of negative controls (bait plasmid alone). Further deletion analysis suggested that the putative coiled-coil region of TRIP mediates the interaction with TRAFs, since a mutant TRIP lacking the N-terminal RING finger motif still inter-acted with TRAFs (residues 56–275 in FIGS. 2A–2B). In addi-tion, both TRIP residues 56–185 and 186–275 interacted with TRAFs, suggesting that TRIP contains two independent TRAF-binding sites within the long coiled-coil domain of the protein.

Figure 4B:
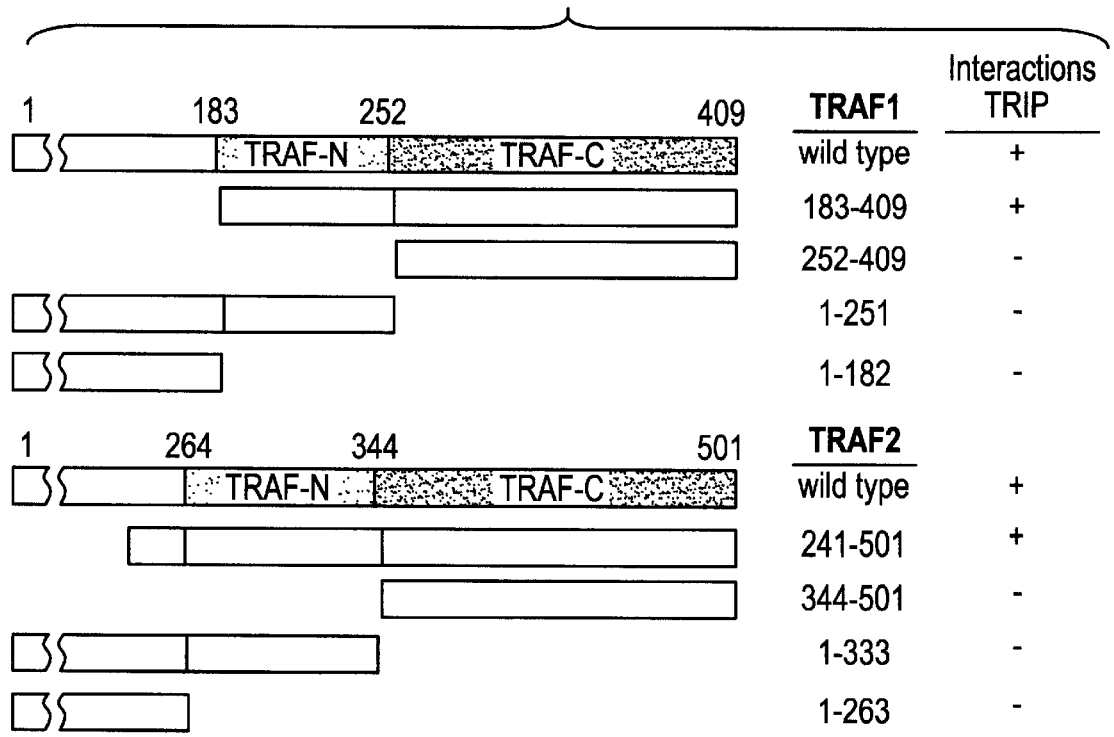
FIG. 4B is a map showing the interaction of TRIP with TRAFs.

To delineate a region in TRAF that is required for TRIP binding, the interaction of TRIP with various truncation mutants of TRAF1 or TRAF2 was determined by the yeast two-hybrid assay or by a transfection-based coprecipitation assay in 293 cells. FIG. 4B shows the interaction of TRIP with TRAFs. Expression vectors encoding the N-terminal deletion mutants of TRAF fused to the LexA DNA binding-domain were cotransformed into yeast with plasmids expressing TRIP fused to the transcription activation domain. Interactions between fusion proteins were scored by measuring b-gal activity of yeast transformants as described in conjunction with FIG. 4A. For the analysis of the C-terminal deletion mutants of TRAFs a transient transfection-based coprecipitation experiment was used. The indicated C-terminal deletion mutants of TRAFs were coexpressed with GST-TRIP fusion proteins in 293 cells. Cell lysates were subjected for purification with glutathione-Sepharose beads, followed by Western blot analysis with anti-TRAF1 or anti-TRAF2 polyclonal antibodies as described in conjunction with FIG. 1.

As shown in FIG. 4B, TRIP interacted with an N-terminal deletion mutant of TRAF1 expressing the entire TRAF domain [TRAF1(183–409)], but failed to interact with an N-terminal deletion mutant of TRAF1 expressing only the TRAF-C domain [TRAF1(252–409)]. TRIP did not interact with a C-terminal deletion mutant of TRAF1 lacking the TRAF-C domain [TRAF1(1–251)], suggesting that the interaction of TRIP with TRAF1 requires the entire TRAF domain. Mutational analysis of TRAF2 also showed that TRIP interacts with TRAF2 through the TRAF domain.

TRIP did not directly interact with the cytoplasmic domains of TNFR2 or CD30 in a yeast two-hybrid assay. However, since the interaction of TRAFs with the cognate members of the TNFR superfamily is mediated through the TRAF-C domain rather than the entire TRAF domain, it was important to determine whether TRIP can indirectly interact with the receptors through TRAFs. To test this, an HA epitope tagged-TRIP and GST-fusion proteins with the cytoplasmic domains of TNFR2 (GST-TNFR2) or CD30 (GST-CD30) were co-expressed in 293 cells in the presence or absence of TRAF. Cell lysates were precipitated with glutathione-Sepharose beads, and analyzed on Western blots with anti-HA, anti-TRAF1, and anti-TRAF2 antibodies. Consistent with the yeast two-hybrid assay, TRIP was not coprecipitated by the GST-TNFR2 or GST-CD30.

Figure 5:
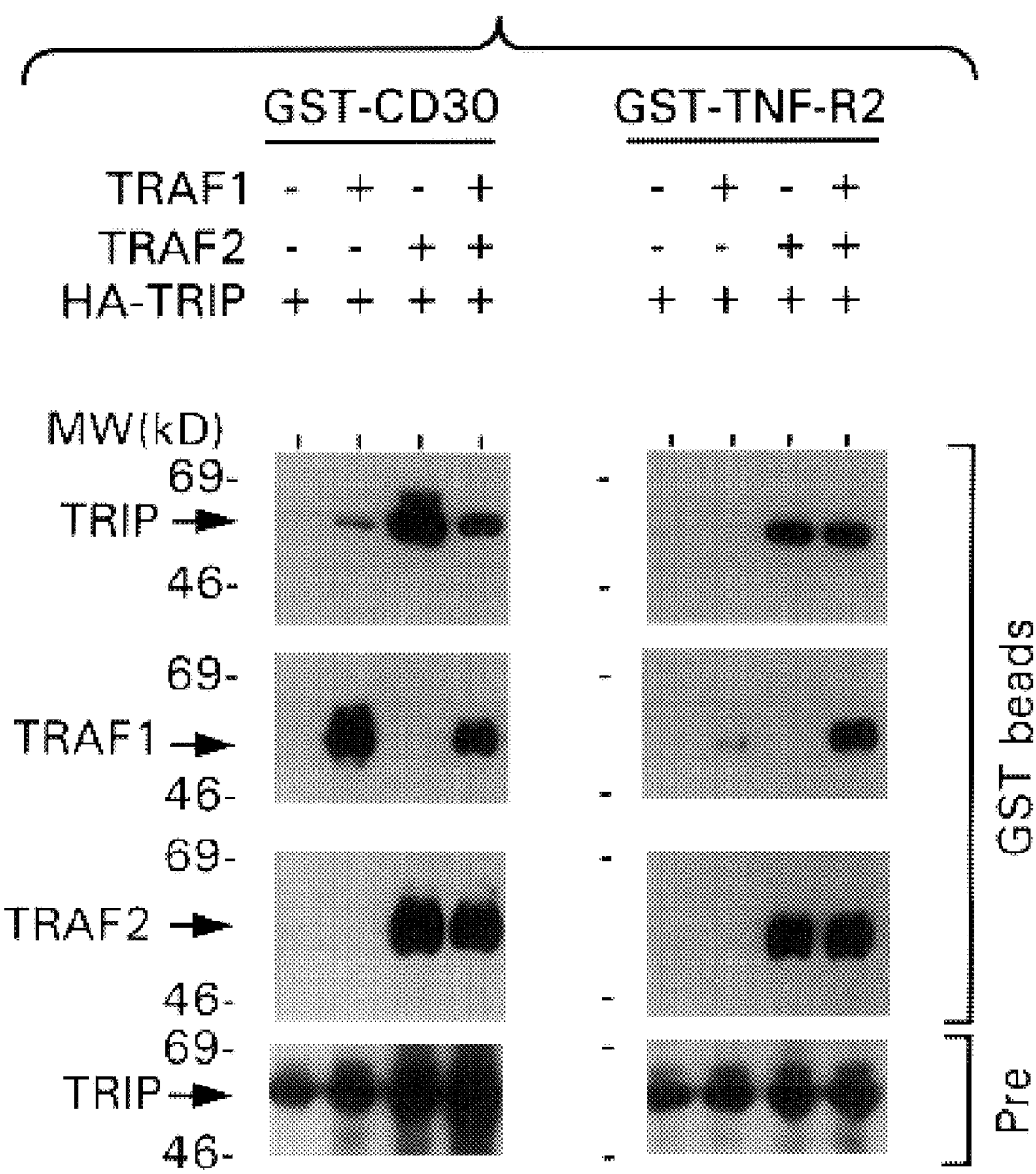
FIG. 5 shows the results of Western analysis of purified cell lysates from transfection assays.

FIG. 5 shows the results of 293 cells transiently transfected with the indicated combinations of equal amounts of HA-TRIP, TRAF1, TRAF2, GST-CD30, or GST-TNFR2 expression vectors for thirty-six hours. Aliquots of cell lysates were subjected for purification with glutathione-Sepharose beads as described in Experimental Procedures. Proteins co-precipitated with GST-fusion proteins were analyzed by Western analysis with an anti-HA mAb (12CA5), and anti-TRAF1- or anti-TRAF2-polyclonal antibodies. In control experiments, GST proteins did not coprecipitate any of the proteins tested.

FIG. 5 also shows that cell lysates prior to purification with glutathione-Sepharose beads were analyzed by Western analysis with anti-TRIP polyclonal antibodies to reveal that equal amounts of TRIP was expressed in each case. The positions of molecular mass markers are shown on the left. Arrows indicating the positions of TRAF1, TRAF2 or TRIP are also shown on the left. When TRAF2 was coexpressed, TRIP was readily co-precipitated by the GST-TNFR2. GST-TNFR2, which does not strongly interact with TRAF1 oligomer, did not readily co-precipitate the TRAF1-TRIP complex. Coexpression of both TRAF2 and TRAF1 did not increase the amount of TRIP coprecipitated with GST-TNFR2. Similar to GST-TNFR2, GST-CD30 also coprecipitated TRIP efficiently in the presence of TRAF2. Although TRAF1 homo-oligomer can interact with CD30 or TRIP efficiently in 293 cells, only low level of TRIP was coprecipitated by GST-CD30 in the presence of TRAF1 alone. Taken together, these results show that TRIP can be recruited to the TNFR2 or CD30 through the TRAF2 homo-oligomer.

The effect of TRIP expression on TRAF2-mediated NF-kB-dependent reporter gene activation was demonstrated using a transient transfection assay. When overexpressed, TRIP significantly inhibited TRAF2-mediated NF-kB activation. This inhibition was similar to that exerted by overexpression of a dominant negative form of TRAF2 [TRAF2(241–50)].

Figure 6A:
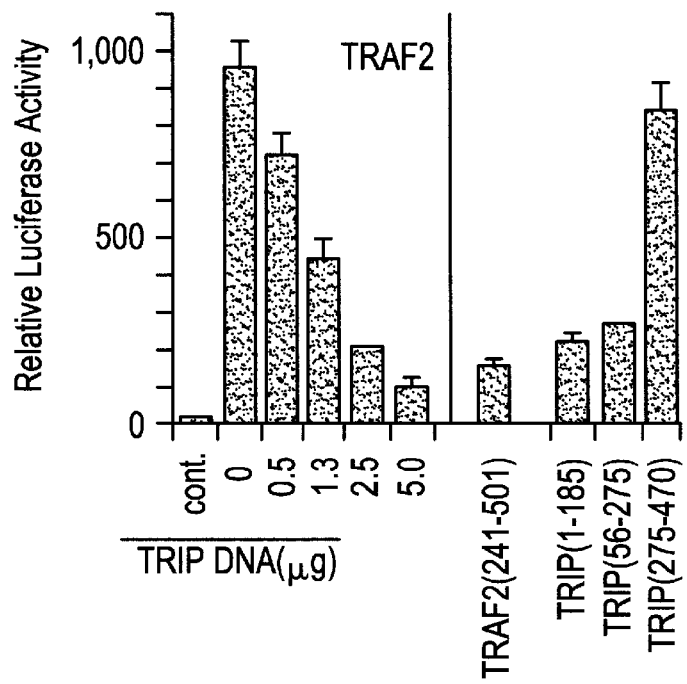
FIG. 6A is a chart depicting the dose-dependent effect of TRIP expression on TRAF2-mediated NF-kB activation.

FIG. 6A, in its left panel, shows a dose-dependent effect of TRIP expression on TRAF2-mediated NF-kB activation. As before, 293 cells were transfected with 0.5 ug of TRAF2 expression vector together with 0.5 ug of p(kB)$_3$-IFN-LUC in the presence of the indicated amount of TRIP expression vectors. Control experiment was transfected with 0.5 ug of pcDNA3.1 control vector and 0.5 ug of p(kB)$_3$-IFN-LUC. All the transfections included 0.25 ug of pCMV-bgal plasmids. After forty-eight hours posttransfection, cell lysates were prepared and used for luciferase assay. All values represent luciferase activities normalized to b-galactosidase activities and are shown as means with their respective SEMs for representative experiments performed in duplicate.

FIG. 6A, in its right panel, shows that the putative coiled-coil domain of TRIP is required to inhibit TRAF2-mediated NF-kB activation. As before, 293 cells were transfected with 0.5 ug of TRAF2 expression vector together with 0.5 ug of p(kB)$_3$-IFN-LUC in the presence of 5 ug of plasmids expressing a dominant negative form of TRAF2 [TRAF2(241–501)], or expressing the indicated TRIP mutants. For the control experiment, cells were transfected with 0.5 ug of pcDNA3.1 control vector and 0.5 ug of p(kB)$_3$-IFN-LUC. All the transfections included 0.25 mg of pCMV-bgal plasmids. Forty-eight hours posttransfection, cell lysates were prepared and used luciferase assay. All values represent luciferase activities normalized to b-galactosidase activities and are shown as means with their respective SEMs for representative experiments performed in duplicate. Luciferase activity of the control experiments is shown in the left panel.

The inhibition of NF-kB activation by TRIP required the same domains of TRIP which mediates the interaction. An N-terminal deletion mutant of TRIP which lacks the TRIP-TRAF interaction domain (residues 275–470 in FIGS. 2A–2B) failed to inhibit TRAF2-mediated NF-kB activation. Moreover, a C-terminal deletion mutant of TRIP containing the N-terminal RING finger motif and the putative coiled-coil domain (residues 1–185 in FIGS. 2A–2B) was sufficient to inhibit TRAF2-mediated NF-kB activation. However, further deletion analysis showed that the RING finger motif of TRIP was not required for inhibition of TRAF2-mediated NF-kB activation because a mutant TRIP containing only the putative coiled-coil domain (residues 56–275 in FIGS. 2A–2B) was sufficient to inhibit TRAF2-mediated NF-kB activation. Overexpression of a mutant TRIP expressing only the N-terminal RING finger motif failed to inhibit NF-kB activation. These results suggested that the coiled-coil domain of TRIP (residues 56–275 in FIGS. 2A–2B) (SEQ ID NO: 3) (SEQ ID NO: 4) is required for TRIP-TRAF interaction and also for inhibition of TRAF2-mediated NF-kB activation.

Figure 6B:
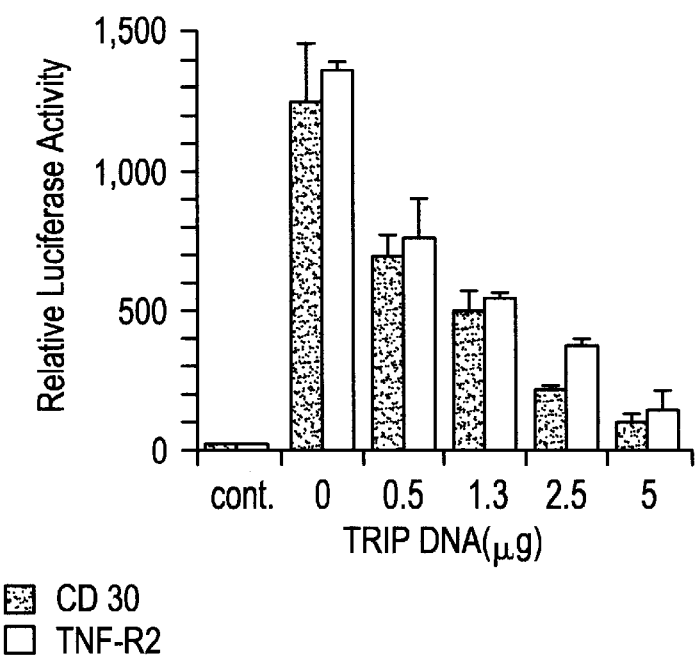
FIG. 6B shows the dose-dependent inhibition of TNFR2- or CD30-mediated NF-kB activation by TRIP.

Since TRIP associates with the receptor complex, the effect of TRIP on NF-kB activation induced via TNFR2 or CD30 was also tested. As previously shown, overexpression of chimeric receptors with the extracellular domain of CD8 fused to the cytoplasmic domain of TNFR2 (CD8-TNFR2) or CD30 (CD8–CD30) induced NF-kB activation in 293 cells without further crosslinking. This is similar to the activation of NF-kB induced by overexpression of wild-type TNFR2, CD40 or other chimeric receptors in 293 cells, which will trigger the clustering of signal transducers without additional cross-linking by cognate ligands or antibodies. When TRIP was co-expressed, the receptor-mediated NF-kB activation was significantly inhibited. FIG. 6B demonstrates dose-dependent inhibition of TNFR2- or CD30-mediated NF-kB activation by TRIP. The 293 cells were transfected with 1 ug of plasmids expressing the chimeric receptors, CD8-TNFR2 or CDB-CD30, together with 0.5 ug of p(kB)$_3$-IFN-LUC in the presence of the indicated amount of TRIP expression vectors. For the control experiment, cells were transfected with 0.5 ug of pcDNA3.1 control vector and 0.5 ug of p(kB)$_3$-IFN-LUC. All the transfections included 0.25 ug of pCMV-βgal plasmids. All values represent luciferase activities normalized to β-galactosidase activities and are shown as means with their respective SEMs for representative experiments performed in duplicate. Because NF-kB activation by TNFR2 and CD30 is mediated by TRAF2 the results are consistent with that TRIP works as a proximal negative regulator of TRAF2-mediated NF-kB activation by members of the TNFR superfamily.

Since TRAF2 also mediates NF-kB activation triggered by the TNFR1-TRADD complex, the effect of TRIP overexpression on TNF-induced NF-kB activation in 293 cells, which is mediated by TNFR1, was studied. Overexpression of TRIP in 293 cells inhibited TNF-induced NF-kB activation. Consistent with this, TRIP overexpression also inhibited NF-kB activation mediated by TRADD overexpression in 293 cells.

Figure 6C:
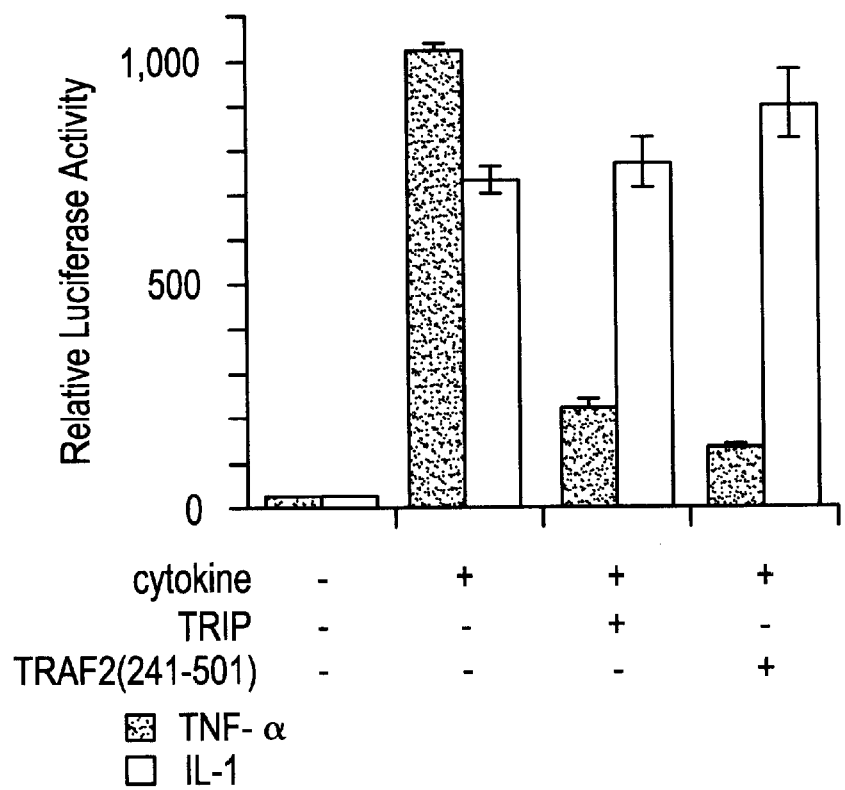
FIG. 6C demonstrates TRIP overexpression and inhibition of TNF-induced NF-kB activation.

FIG. 6C demonstrates that TRIP overexpression inhibits TNF-induced NF-kB activation. The 293 cells were transfected with 0.5 ug of p(kB)$_3$-IFN-LUC in the presence or absence of 5 ug of plasmids expressing a dominant negative form of TRAF2 [TRAF2(241–501)], or TRIP. For the control experiment, cells were transfected with 0.5 ug of pcDNA3.1 control vector and 0.5 ug of p(kB)$_3$-IFN-LUC. All the transfections included 0.25 ug of pCMV-bgal plasmids. Thirty-six hours post-transfection, cells were treated for six hours with 100 pg/ml of either TNF or IL-1. All values represent luciferase activities normalized to b-galactosidase activities and are shown as means with their respective SEMs for representative experiments performed in duplicate.

Figure 6D:
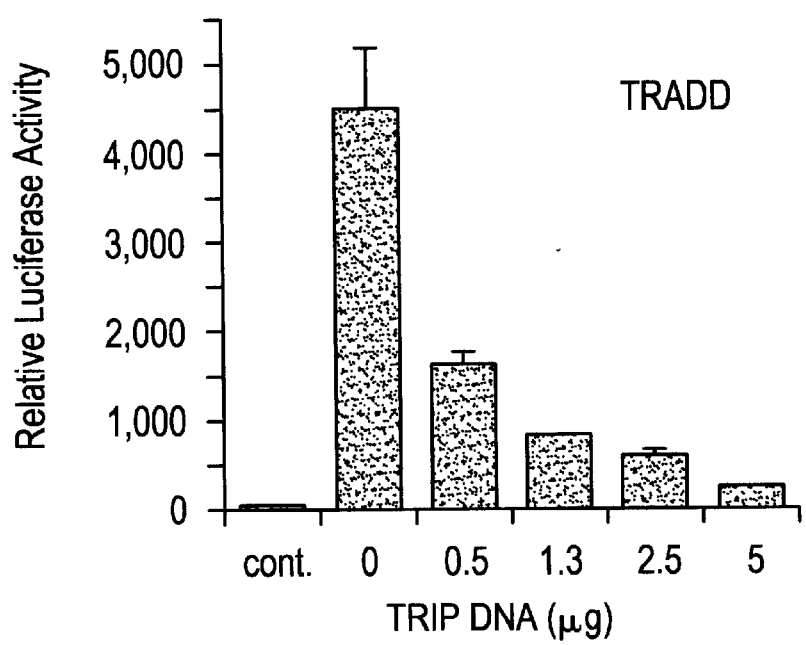
FIG. 6D demonstrates TRIP overexpression and inhibition of TRADD-mediated NF-kB activation.
Figure 7:
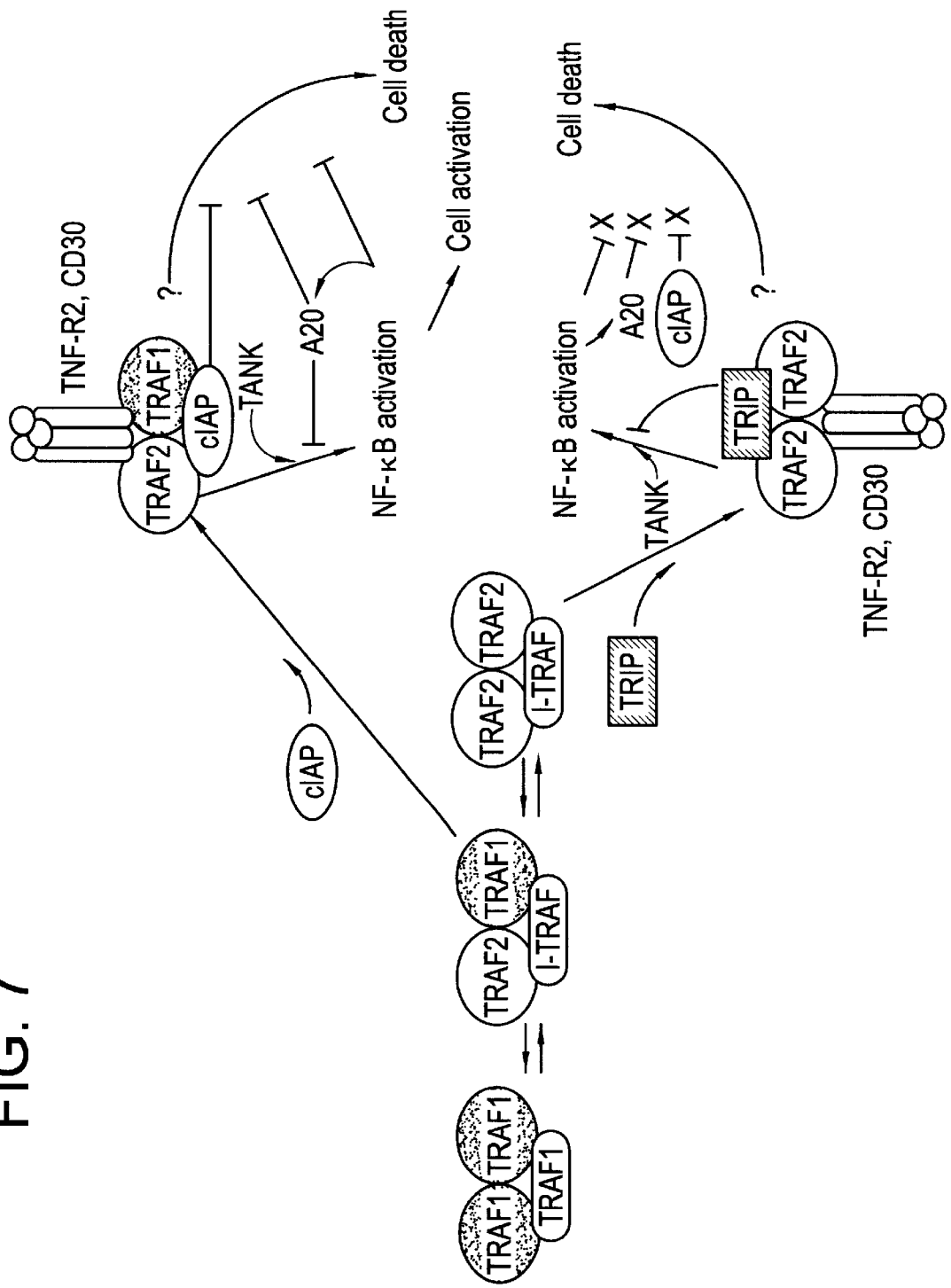
FIG. 7 is a schematic representation of the inter-relationship of TRAFs, c-IAPs and TRIP, and the switch of the TRAF-mediated signals between cell activation and cell death.

FIG. 6D shows the results on assays that demonstrated TRIP overexpression inhibits TRADD-mediated NF-kB activation. The 293 cells were transfected with 0.5 ug of plasmids expressing TRADD together with 0.5 ug of p(kB)$_3$-IFN-LUC in the presence of the indicated amounts of TRIP expression vectors. For the control experiment, cells were transfected with 0.5 ug of pcDNA3.1 control vector and 0.5 ug of p(kB)$_3$-IFN-LUC. All the transfections included 0.25 ug of pCMV-bgal plasmids. All values represent luciferase activities normalized to b-galactosidase activities and are shown as means with their respective SEMs for representative experiments performed in duplicate.

Whereas TRAF2 is required for TNF- or TRADD-induced NF-kB activation, it is not required for NF-kB activation induced by IL-1 in 293 cells. To test whether TRIP affects TRAF2-mediated NF-kB activation specifically, the effect of TRIP overexpression on NF-kB activation by IL-1 was also tested as noted above. In contrast to TNF-induced NF-kB activation, IL-1-induced NF-kB activation was not inhibited by TRIP overexpression. Recent experiments have shown that IL-1-induced NF-kB activation is mediated by another member of the TRAF family, TRAF6. These results suggest that TRIP is a specific inhibitor of TRAF2-mediated NF-kB activation, rather than a general inhibitor of NF-kB activation.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

---

What is claimed is:

1. A regulator capable of binding to TRAF2 having an amino acid sequence selected from the group consisting of the full sequences shown in FIG. 2A (SEQ ID NO: 1) (SEQ ID NO:2), a fragment thereof, an allelic variation thereof, a homologous analog thereof and a mutein thereof.

2. The regulator of claim 1 which is derived from mammalian cells.

3. The regulator of claim 1 labeled with a detectable label.

4. The regulator of claim 3 wherein the label is selected from the group consisting of enzymes, chemicals which fluoresce and radioactive elements.

5. The regulator of claim 1 capable of inhibiting NF-KB activation.

6. The regulator of claim 1, wherein said fragment has an amino acid sequence selected from the group consisting of residue numbers 56 through 275 shown in FIG. 2A (SEQ ID NO:3) (SEQ ID NO:4) and fragments thereof.

7. The fragment of claim 6 labeled with a detectable label.

8. The fragment of claim 7 wherein the label is selected from the group consisting of enzymes, chemicals which fluoresce and radioactive elements.

9. The polypeptide as set forth in SEQ ID NO:1.

10. The polypeptide as set forth in SEQ ID NO:2.

11. The polypeptide as set forth in SEQ ID NO:3.

12. The polypeptide as set forth in SEQ ID NO:4.

* * * * *